(12) United States Patent
Matsunaga et al.

(10) Patent No.: US 11,975,326 B2
(45) Date of Patent: May 7, 2024

(54) CELL ACCOMMODATING CHIP AND SCREENING METHOD USING THE CELL ACCOMMODATING CHIP

(71) Applicant: YAMATO SCIENTIFIC CO., LTD., Tokyo (JP)

(72) Inventors: Mariko Matsunaga, Tokyo (JP); Ken Tsukii, Tokyo (JP); Kenichi Kimura, Tokyo (JP); Toru Takahashi, Tokyo (JP); Jie Xu, Tokyo (JP)

(73) Assignee: YAMATO SCIENTIFIC CO., LTD., Tokyo (JP)

( * ) Notice: Subject to any disclaimer, the term of this patent is extended or adjusted under 35 U.S.C. 154(b) by 639 days.

(21) Appl. No.: 16/146,792

(22) Filed: Sep. 28, 2018

(65) Prior Publication Data

US 2019/0039070 A1 Feb. 7, 2019

Related U.S. Application Data

(63) Continuation of application No. PCT/JP2017/013560, filed on Mar. 31, 2017.

(30) Foreign Application Priority Data

Mar. 31, 2016 (JP) .................. 2016-070969

(51) Int. Cl.
*B01L 3/00* (2006.01)
*C12M 1/00* (2006.01)
(Continued)

(52) U.S. Cl.
CPC ... *B01L 3/502753* (2013.01); *B01L 3/502715* (2013.01); *B01L 3/50855* (2013.01);
(Continued)

(58) Field of Classification Search
CPC ......... B01L 3/502753; B01L 3/502715; B01L 3/50855; B01L 2300/161; B01L 2300/168;
(Continued)

(56) References Cited

U.S. PATENT DOCUMENTS 4,495,289 A 1/1985 Lyman et al.
5,776,748 A * 7/1998 Singhvi .................. C12N 5/067
435/395
(Continued)

FOREIGN PATENT DOCUMENTS

CN 1553188 A 12/2004
CN 1771438 A 5/2006
(Continued)

OTHER PUBLICATIONS

Rios, et. al.; Biochemically Responsive Smart Surface; ACS Appl Mater Interfaces. Apr. 29, 2009; 1(4): 768-774 (Year: 2009).*
(Continued)

*Primary Examiner* — William H. Beisner
*Assistant Examiner* — Danielle B Henkel
(74) *Attorney, Agent, or Firm* — Birch, Stewart, Kolasch & Birch, LLP

(57) ABSTRACT

A cell accommodating chip capable of accommodating a plurality of cells includes a substrate composed of a light-transmitting material, and a plurality of wells on at least one of main faces of the substrate, the plurality of wells being capable of accommodating cells. A surface of the cell accommodating chip including the plurality of wells has a low cell adhesion property, and affinity to a specific binding material having affinity to a produced substance produced by a cell accommodated in one of the wells and/or a released substance released by the cell.

24 Claims, 12 Drawing Sheets

(51) Int. Cl.
*C12M 1/26* (2006.01)
*C12M 1/32* (2006.01)
*C12M 1/34* (2006.01)
*G01N 33/48* (2006.01)
*G01N 33/50* (2006.01)

(52) U.S. Cl.
CPC ............ *C12M 23/12* (2013.01); *C12M 23/20* (2013.01); *C12M 23/22* (2013.01); *C12M 33/04* (2013.01); *C12M 41/36* (2013.01); *G01N 33/48* (2013.01); *G01N 33/5005* (2013.01); *B01L 2300/161* (2013.01); *B01L 2300/168* (2013.01)

(58) Field of Classification Search
CPC ...... C12M 23/12; C12M 23/20; C12M 23/22; C12M 33/04; C12M 41/36; G01N 33/5005; G01N 33/48
See application file for complete search history.

(56) References Cited

U.S. PATENT DOCUMENTS

| | | | |
|---|---|---|---|
| 6,270,983 B1 * | 8/2001 | Strohner | G01N 33/54393 530/367 |
| 8,323,973 B2 | 12/2012 | Kanome et al. | |
| 8,518,714 B2 * | 8/2013 | Soldo | G01N 33/54393 435/7.5 |
| 9,494,575 B2 | 11/2016 | Jin et al. | |
| 11,339,407 B2 * | 5/2022 | Waters | C12M 45/05 |
| 2003/0022216 A1 | 1/2003 | Mao et al. | |
| 2003/0219816 A1 | 11/2003 | Solomon et al. | |
| 2005/0014201 A1 | 1/2005 | Deuthsch | |
| 2006/0147949 A1 | 7/2006 | Ha et al. | |
| 2007/0105089 A1 | 5/2007 | Deutsch | |
| 2007/0148698 A1 | 6/2007 | Solomon et al. | |
| 2007/0148783 A1 | 6/2007 | Solomon et al. | |
| 2008/0175758 A1 | 7/2008 | Matsumoto et al. | |
| 2009/0191626 A1 | 7/2009 | Shogbon et al. | |
| 2011/0189721 A1 | 8/2011 | Deutsch | |
| 2011/0212853 A1 | 9/2011 | Cynis et al. | |
| 2011/0294678 A1 * | 12/2011 | Jin | G01N 33/54366 506/9 |
| 2012/0015824 A1 | 1/2012 | Love et al. | |
| 2012/0059111 A1 | 3/2012 | Sandhu et al. | |
| 2014/0011960 A1 | 1/2014 | Konno et al. | |
| 2014/0018260 A1 * | 1/2014 | Zhang | C40B 20/02 506/10 |
| 2014/0134729 A1 | 5/2014 | Shogbon et al. | |
| 2015/0017221 A1 | 1/2015 | Hayashi et al. | |
| 2016/0023209 A1 | 1/2016 | Lenigk et al. | |
| 2016/0168294 A1 | 6/2016 | Hayashi et al. | |
| 2016/0333313 A1 | 11/2016 | Shogbon et al. | |
| 2016/0369123 A1 | 12/2016 | Takada et al. | |
| 2016/0370342 A1 | 12/2016 | Kimura et al. | |
| 2017/0023562 A1 | 1/2017 | Jin et al. | |
| 2018/0023053 A1 | 1/2018 | Shogbon et al. | |
| 2019/0048113 A1 | 2/2019 | Hayashi et al. | |
| 2019/0338246 A1 | 11/2019 | Shogbon et al. | |

FOREIGN PATENT DOCUMENTS

| | | |
|---|---|---|
| CN | 1957093 A | 5/2007 |
| CN | 101939362 A | 1/2011 |
| CN | 103209717 A | 7/2013 |
| CN | 103403140 A | 11/2013 |
| CN | 104039949 A | 9/2014 |
| EP | 2 184 345 A1 | 5/2010 |
| JP | 2004-531390 A | 10/2004 |
| JP | 2006-176720 A | 7/2006 |
| JP | 2006-299045 A | 11/2006 |
| JP | 4148367 B1 | 9/2008 |
| JP | 2012-52843 A | 3/2012 |
| JP | 2012-93290 A | 5/2012 |
| JP | 2012-511155 A | 5/2012 |
| JP | 2013-519891 A | 5/2013 |
| JP | 2013-247926 A | 12/2013 |
| JP | 5614179 B2 | 10/2014 |
| WO | WO 03/035824 A1 | 5/2003 |
| WO | WO 2015/133337 A1 | 9/2015 |
| WO | WO 2015/151881 A1 | 10/2015 |

OTHER PUBLICATIONS

Williams, et. al.; Immobilization of streptavidin on 4H-SiC for biosensor development; Applied Surface Science 258 (2012) 6056-6063 (Year: 2012).*
Extended European Search Report dated Oct. 14, 2019 for Application No. 17775525.3.
International Search Report (PCT/ISA/210) issued in PCT/JP2017/013560, dated Jul. 4, 2017.
Written Opinion of the International Searching Authority (PCT/ISA/237) issued in PCT/JP2017/013560, dated Jul. 4, 2017.
Extended European Search Report issued in European Patent Application No. 17775524.6, dated Jan. 3, 2020.
Japanese Office Action, dated Nov. 18, 2020 for corresponding Japanese Application No. 2018-509649, with an English translation.
Non-Final Office Action dated Apr. 14, 2020, issued in corresponding U.S. Appl. No. 16/146,764.
International Preliminary Report on Patentability and the English translation of the Written Opinion of the International Searching Authority (Forms PCT/IB/326, PCT/IB/373 and PCT/ISA/237), dated Oct. 11, 2018 for International Application No. PCT/JP2017/013560.
Japanese Office Action for corresponding Japanese Application No. 2018-509650, dated Jan. 18, 2021, with English translation.
Japanese Office Action, dated Aug. 3, 2021, for corresponding Japanese Application No. 2018-509649, with an English machine translation.
Chinese Office Action for corresponding Chinese Application No. 201780021391.7, dated Nov. 8, 2021, with English translation.
Non-Final Office Action, dated Nov. 2, 2021, issued in corresponding U.S. Appl. No. 16/146,764.
Chinese Office Action and Search Report for Chinese Application No. 201780021248.8, dated Nov. 26, 2021, with an English translation.
International Preliminary Report on Patentability and Written Opinion of the International Searching Authority (Forms PCT/IB/373 and PCT/ISA/237) for International Application No. PCT/JP2017/013561, dated Oct. 2, 2018, with an English translation.
International Search Report (Form PCT/ISA/210) for International Application No. PCT/JP2017/013561, dated Jun. 20, 2017, with an English translation.
Li et al., "Concise Dictionary of Natural Sciences," Compiled by: Editorial Board of Concise Dictionary of Natural Sciences, Shandong University Press, Sep. 1988, 70 pages total, with a partial English translation.
Liu et al., "Introduction to Molecular Ecology," Harbin Institute of Technology Press, Mar. 2012, 23 pages total, with a partial English translation.
U.S. Office Action for U.S. Appl. No. 16/146,764, dated Apr. 14, 2022.
Chinese Office Action and Search Report for corresponding Chinese Application No. 201780021248.8, dated May 14, 2021 with English translation of the Office Action.
Chinese Office Action and Search Report for corresponding Chinese Application No. 201780021391.7, dated May 27, 2021 with English translation of the Office Action.
Chinese Office Action for Chinese Application No. 201780021391.7, dated Apr. 22, 2022, with English translation.
Chinese Office Action for Chinese Application No. 201780021248.8, dated May 7, 2022, with English translation.

* cited by examiner

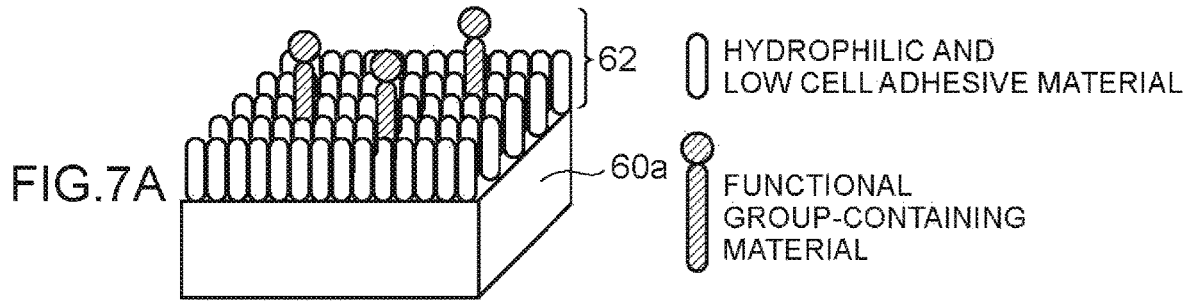
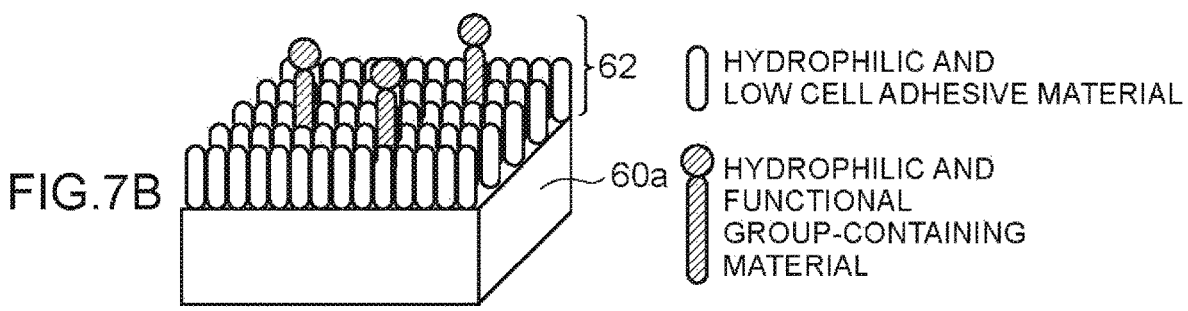
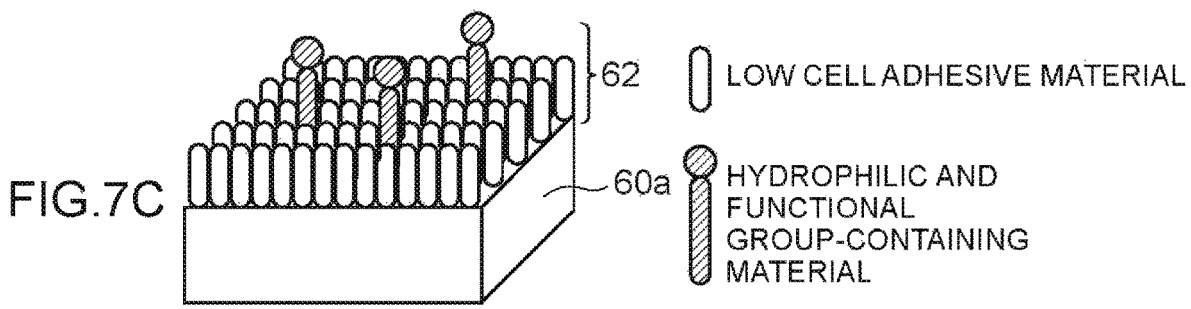
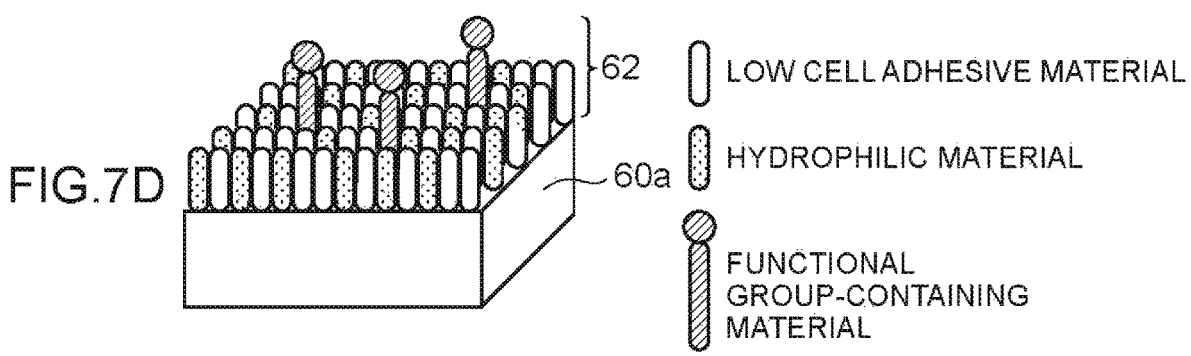
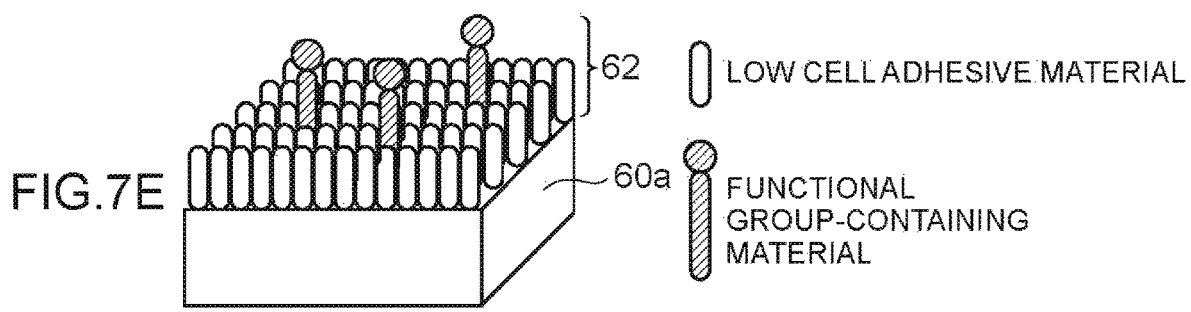

CELL ACCOMMODATING CHIP AND SCREENING METHOD USING THE CELL ACCOMMODATING CHIP

CROSS REFERENCE TO RELATED APPLICATIONS

This is a continuation application of International Patent Application No. PCT/JP2017/013560 filed Mar. 31, 2017, which claims the benefit of Japanese Patent Application No. 2016-070969, filed Mar. 31, 2016, the full contents of both of which are hereby incorporated by reference in their entirety.

BACKGROUND

Technical Field

The present disclosure relates to a cell accommodating chip capable of accommodating a plurality of cells in screening for a target sample and a screening method using the cell accommodating chip, and particularly relates to a cell accommodating chip for detecting a cell to be a target sample by irradiating wells and cells with light and based on fluorescence emitted by a substance bound on the cell accommodating chip and selectively sucking and collecting the cell, as well as a screening method using the cell accommodating chip.

Background

In the related art, screening apparatuses have been widely used as apparatuses for identifying and isolating minute analytes, such as cells, in research, inspection, and so on in the medical field. In recent years, in the research and inspection institutions, there are demands for achieving identification and isolation without destroying analytes and for increasing the efficiency of research and inspection by more exactly performing these treatments. In particular, in a predetermined field, since there is a growing demand for identifying and isolating, on a single cell basis, a specific cell from a large number of cells, improvement of accuracy and enhancement of efficiency are required also in such identification and isolation treatments on a single cell basis.

In identification and isolation treatments of cells performed with a nondestructive manner, it is desirable to retain a medium containing a large number of fine particles on a cell accommodating chip such that a target sample and a nontarget sample are clearly distinguished from each other. Accordingly, in the related art, for example, a method for identifying a target sample using a microwell array chip including a coating layer prepared by binding an anti-immunoglobulin (Ig) antibody to a part of an upper surface of the chip, dispensing an antibody-secreting cells to each well of the microwell array chip to bind an antibody secreted from at least some of the cells accommodated in the well to the anti-Ig antibody of the coating layer, and detecting the secreted antibody with a fluorescence-labeled antigen is disclosed (Japanese Patent No. 4148367).

In addition, in order to selectively bind a desired target sample from an external environment or collectively remove nontarget samples from a surface, a functional coating prepared by supplying, to a plate-like support, a low non-specific binding matrix immobilized on the support and an active component covalently bonded in the nonspecific binding matrix by physically entangling is disclosed (National Publication of International Patent Application No. 2004-531390).

However, with the technique of Japanese Patent No. 4148367, since the chip upper surface must be kept wet during the period from binding of an anti-Ig antibody to a part of the chip upper surface until identification of the target sample, the anti-Ig antibody cannot be sustained for a long time. In addition, since a cell may adhere to an inner surface of a well during antibody secretion by the cell, it is difficult to collect the cell, and even if the cell was collected, it is very likely to damage the cell that is a target sample.

In addition, National Publication of International Patent Application No. 2004-531390 discloses a structure in which a target sample is selectively bound to a functional coating disposed on an upper surface of a plate-like support, but not a structure retaining a single cell in each well, and it cannot be said that the accuracy and efficiency of identification and isolation of a specific cell on a cell basis are high.

The present disclosure is related to providing a cell accommodating chip that can identify and isolate a target sample with high accuracy and high efficiency, that can be simply handled, and that allows easy collection without damaging the cell, and to provide a screening method using the cell accommodating chip.

SUMMARY

According to a first aspect of the present disclosure, a cell accommodating chip capable of accommodating a plurality of cells, includes a substrate composed of a light-transmitting material, and a plurality of wells on at least one of main faces of the substrate, the plurality of wells being capable of accommodating cells, a surface of the cell accommodating chip including the plurality of wells having a low cell adhesion property, and affinity to a specific binding material having affinity to a produced substance produced by a cell accommodated in one of the wells and/or a released substance released by the cell.

According to a second aspect of the present disclosure, a screening method for searching for a predetermined cell based on optical information emitted from a substance on a cell accommodating chip and selectively picking up the cell searched for, the method includes: a preparation step of preparing a cell accommodating chip having a plurality of wells disposed on a substrate composed of a light-transmitting material and having a surface having a low cell adhesion property and affinity to a specific binding material having affinity to a produced substance produced by a cell accommodated in one of the wells and/or a released substance released by the cell; a first binding step of binding the specific binding material to the surface of the cell accommodating chip; a cell accommodating step of introducing a liquid containing a plurality of cells to the cell accommodating chip and accommodating the plurality of cells in the plurality of wells on a cell-by-cell basis; a second binding step of binding a produced substance and/or a released substance by the cell accommodated in one of the wells to the specific binding material; a third binding step of binding the produced substance or the released substance or the specific binding material to an optical information-holding substance having optical information; a measurement step of measuring the optical information of the optical information-holding substance; and an identification/collection step of identifying and collecting a cell as a target sample from the plurality of cells based on the measurement result in the measurement step.

According to the present disclosure, a surface of a cell accommodating chip having a plurality of wells has a low cell adhesion property and also has affinity to a specific binding material having affinity to a produced substance that is produced by a cell accommodated in any of the wells and/or a released substance that is released by said cell. Since a chip of the related art has a structure in which a substance having affinity to a produced substance or a released substance is bound on the chip in advance, it is difficult to preserve the chip for a long period of time, and the accuracy may decrease due to drying or the like. In contrast, according to the present disclosure, since the surface of the cell accommodating chip has affinity to the specific binding material, it is not necessary to bind a specific binding material having affinity to a produced substance and/or a released substance on the cell accommodating chip in advance, and a reduction in accuracy due to drying or the like can be prevented. In addition, due to the affinity of the surface of the cell accommodating chip to the specific binding material, the specific binding material binds to the surface of the cell accommodating chip having wells, and a produced substance that is produced by a cell in any of the wells and/or a released substance that is released by said cell binds to the specific binding material. Accordingly, the well itself can be used as a labeling site in identification of a target sample, and the target sample can be identified without damaging the cell. Furthermore, since the surface of the cell accommodating chip has a low cell adhesion property, the cell in the well can be prevented from adhering to the surface of the cell accommodating chip, the cell that is a target sample can be collected at high efficiency without requiring coating treatment using a blocking reagent or the like, and in cell collection, the cell can be collected without being damaged.

In addition, according to the present disclosure, a cell accommodating chip having a surface that has a low cell adhesion property and affinity to a specific binding material having affinity to a produced substance produced and/or a released substance released by a cell accommodated in a well is prepared; and a specific binding material is bound to the surface of the cell accommodating chip, a liquid containing a plurality of cells is introduced to the cell accommodating chip to accommodate the plurality of cells in a plurality of wells on a cell-by-cell basis to bind the produced substance and/or the released substance by the cell accommodated in the well to the specific binding material, which allows the produced substance or released substance or the specific binding material to bind an optical information-holding substance having optical information. It is therefore possible to identify and isolate the target sample with high accuracy and high efficiency. In addition, with simple handling, easy collection can be achieved without damaging the cells during cell collection.

BRIEF DESCRIPTION OF DRAWINGS

FIGS. 7A to 7E are schematic views illustrating examples of the combination of a hydrophilic material, a functional group-containing material, and a low cell adhesive material contained in a coating layer formed on the inner surfaces of the wells shown in FIG. 6.

DETAILED DESCRIPTION

Figure 1:
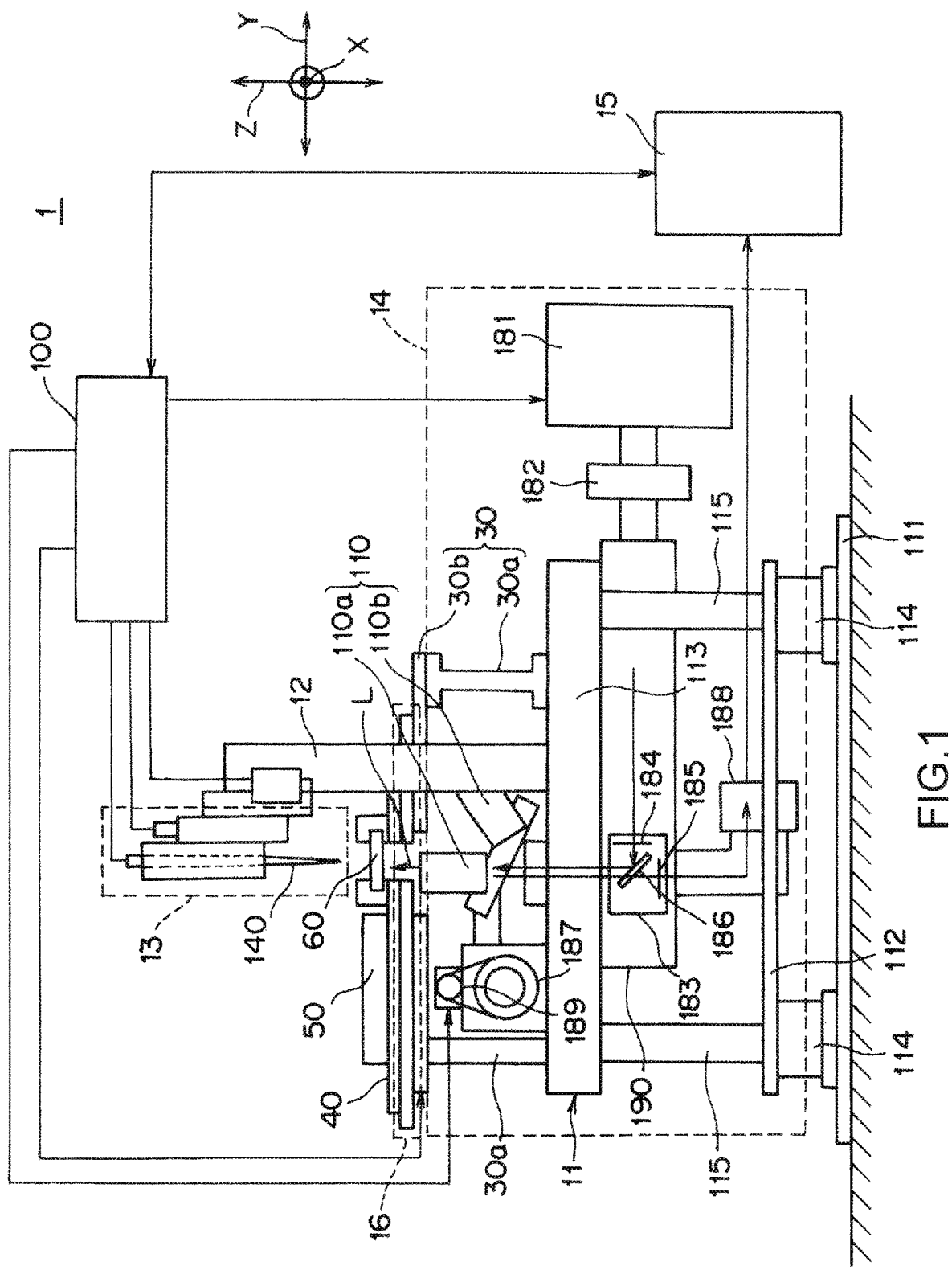
FIG. 1 is a side view schematically illustrating a structure of a screening apparatus according to an embodiment of the present disclosure.

Embodiments of the present disclosure will now be described in detail referring to the drawings.

(Structure of Screening Apparatus)

Figure 2:
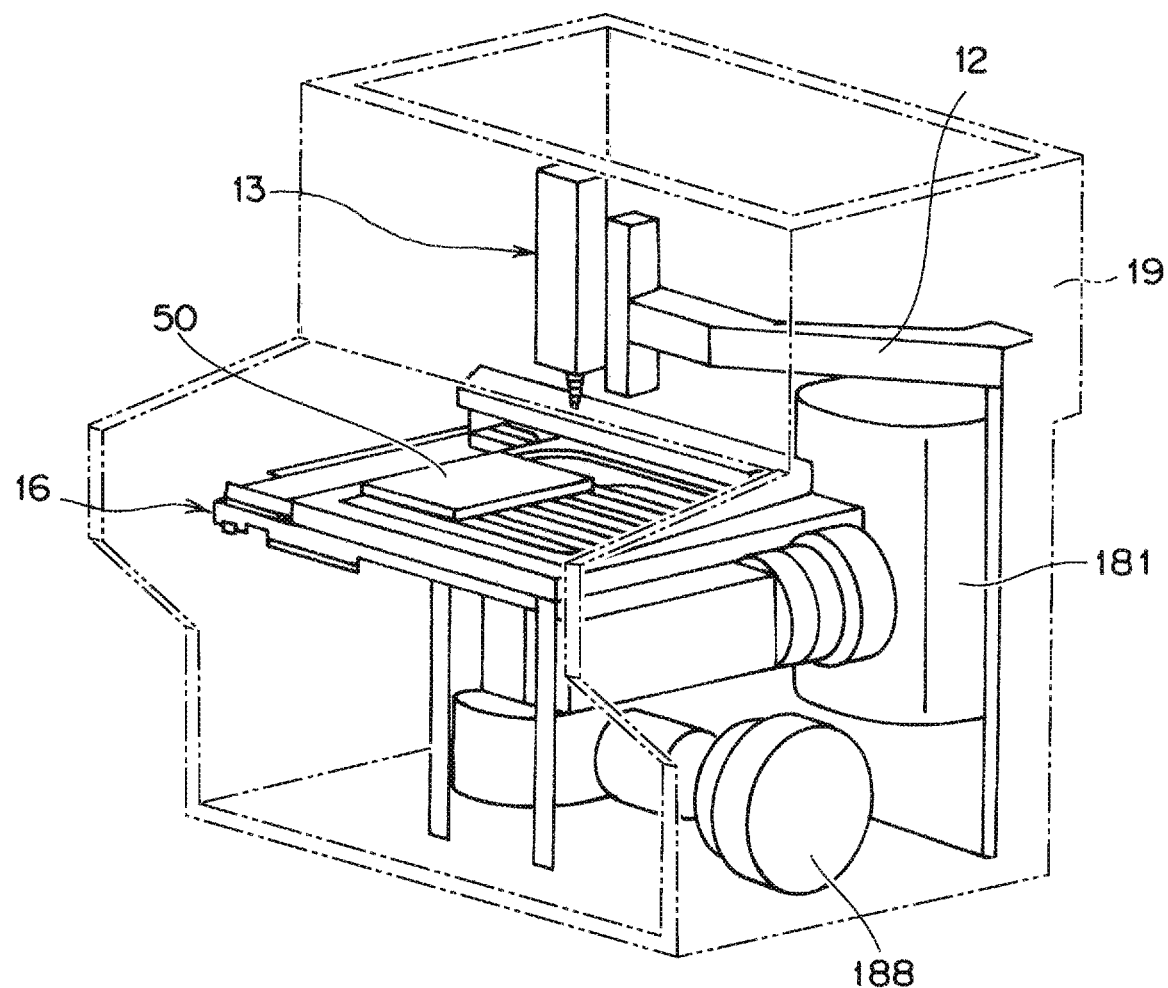
FIG. 2 is a perspective view of the screening apparatus of FIG. 1.

FIG. 1 is a side view schematically illustrating a structure of a screening apparatus according to the present embodiment, and FIG. 2 is a perspective view of the screening apparatus shown in FIG. 1. The screening apparatus shown in FIGS. 1 and 2 is merely an example, and the screening apparatus according to the present disclosure is not limited to that shown in FIGS. 1 and 2. For convenience of explanation, the direction perpendicular to the plane of paper of FIG. 1 is defined as the X-direction, the horizontal direction is defined as the Y-direction, and the direction perpendicular to the X-direction and the Y-direction is defined as the Z-direction.

In FIGS. 1 and 2, the screening apparatus 1 is an apparatus that searches for a predetermined cell as a target sample based on optical information emitted from a plurality of microparticles (e.g., cells of living) in a cell accommodating chip 60, and selectively sucks and picks up a cell in a well that accommodates a cell satisfying a collecting condition to collect the cell in an accommodating plate 50.

Specifically, the screening apparatus 1 includes a base 11, a supporting section 12 (see FIG. 2), a collecting section 13, a measuring section 14, an image analyzing section 15, and a moving section 16, and, as shown in FIG. 2, all the sections are covered with a cover 19 for preventing penetration of light and foreign substances from outside.

The base 11 is a main body frame for holding each element of the screening apparatus 1. This base 11 includes plate members 111, 112, and 113 disposed substantially horizontally and holds the collecting section 13, the measuring section 14, and the moving section 16 via these plate members. The plate members 111 and 112 are fixed parallel to each other by a plurality of vertical members 114, and the plate members 112 and 113 are fixed parallel to each other by a plurality of vertical members 115. The vertical members 114 are made of a material shielding a vibration and are configured to be adjustable in height.

The supporting section 12 and a supporting table 30 are fixed on the plate member 113 located at the uppermost position of the plurality of plate members. The supporting section 12 is arranged on the plate member 113 extending vertically along the Z-direction. The supporting table 30 includes a leg section 30a and a support plate 30b. The plate members 111, 112, and 113 and the support plate 30b are arranged with a predetermined interval therebetween in the Z-direction.

The moving section 16 is mounted and secured on the support plate 30b of the supporting table 30. A mounting table 40, an accommodating plate 50, and a cell accommodating chip 60 are mounted on the moving section 16. The moving section 16 can move and position the mounting table 40, i.e., the accommodating plate 50 and the cell accommodating chip 60 mounted on the mounting table 40, along the X-direction and/or the Y-direction.

Figure 3:
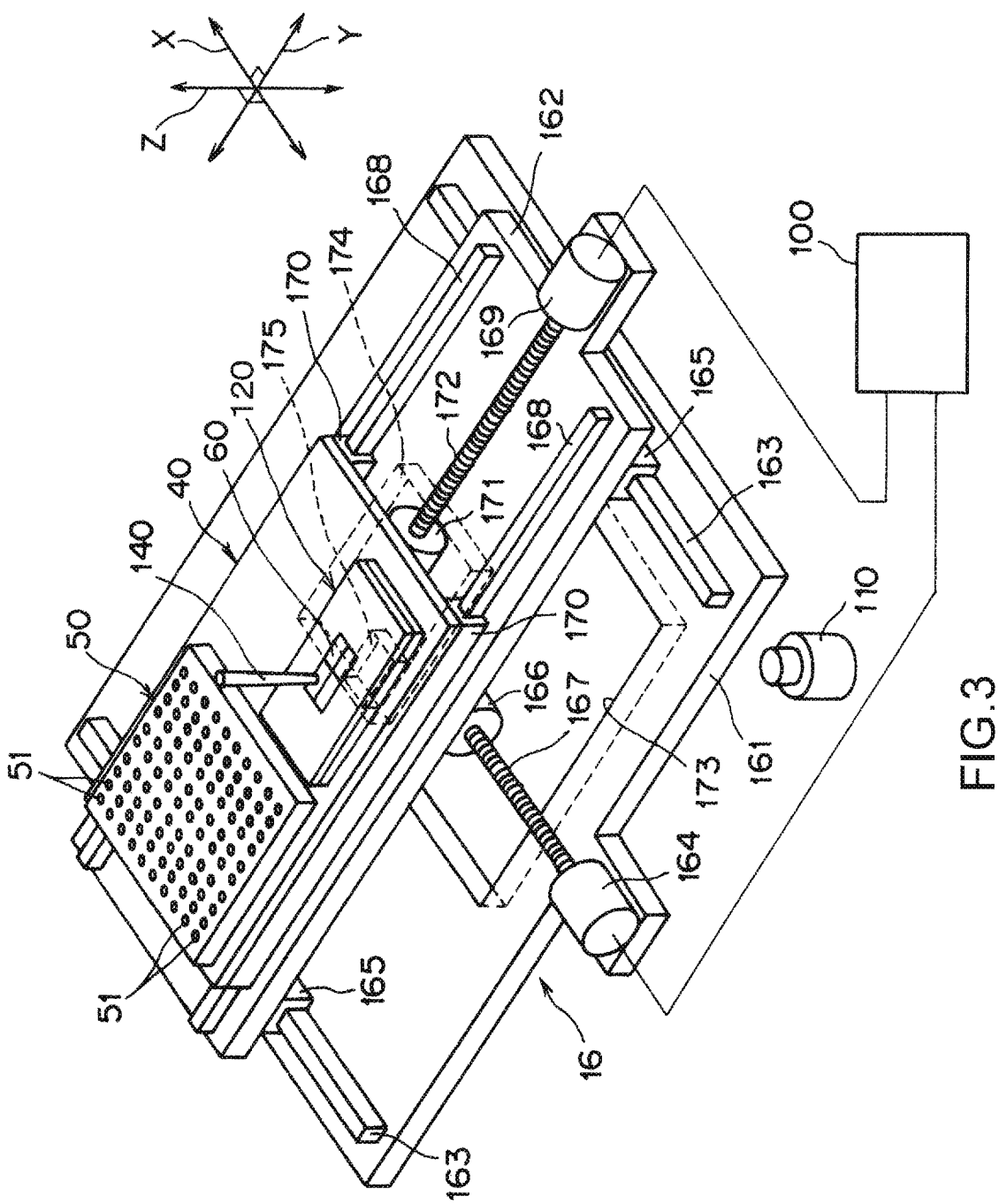
FIG. 3 is a perspective view illustrating details of a moving section and a mounting table shown in FIG. 2.

FIG. 3 is a perspective view illustrating details of the moving section 16 and the mounting table 40 shown in FIG. 2.

As shown in FIG. 3, the moving section 16 includes a table 161 and a table 162 arranged on said table. The table 161 is secured to the supporting table 30 and mounted so as to be capable of moving and positioning the table 162 along the X-direction. The table 162 is mounted so as to be capable of moving and positioning the mounting table 40 along the Y-direction.

Guide rails 163, 163 and a motor 164 are disposed on the upper surface of the table 161. Engaging members 165, 165 having a U-shaped cross section and a nut 166 are disposed on the lower surface of the table 162. The engaging members 165, 165 are movably engaged with the guide rails 163, 163, respectively. A feed screw 167 of the motor 164 is screwed to the nut 166.

The motor 164 is electrically connected to a control unit 100 and is operated in response to a command from the control unit 100 to rotate the feed screw 167. Consequently, the table 162 is moved and positioned along the X-direction.

Guide rails 168, 168 and a motor 169 are disposed on the upper surface of the table 162. Engaging members 170, 170 having a U-shaped cross section and a nut 171 are disposed on the lower surface of the mounting table 40. The engaging members 170, 170 are movably engaged with the guide rails 168, 168, respectively. A feed screw 172 of the motor 169 is screwed to the nut 171.

The motor 164 is electrically connected to the control unit 100 and is operated in response to a command from the control unit 100 to rotate the feed screw 172. Consequently, the mounting table 40 is moved and positioned in the Y-direction.

The table 161 has an opening 173, the table 162 has an opening 174, and the mounting table 40 has an opening 175. These openings 173, 174, and 175 have respective sizes such that the openings always overlap each other even if the table 162 moves in the X-direction and the mounting table 40 moves in the Y-direction. Through these openings 173, 174, and 175, the cells on the cell accommodating chip 60 on the mounting table 40 are irradiated with light L from the objective lens 110 side of the measuring section 14.

In addition, even if the table 162 moves in the X-direction and the mounting table 40 moves in the Y-direction, the light L from the objective lens 110 side passes through the openings 173, 174, and 175 and irradiates the cells on the cell accommodating chip 60 on the mounting table 40. That is, it is possible to generate fluorescence from a cell and/or a well accommodating a cell at any relative position of the tables 161 and 162 and the mounting table 40.

Figure 4:
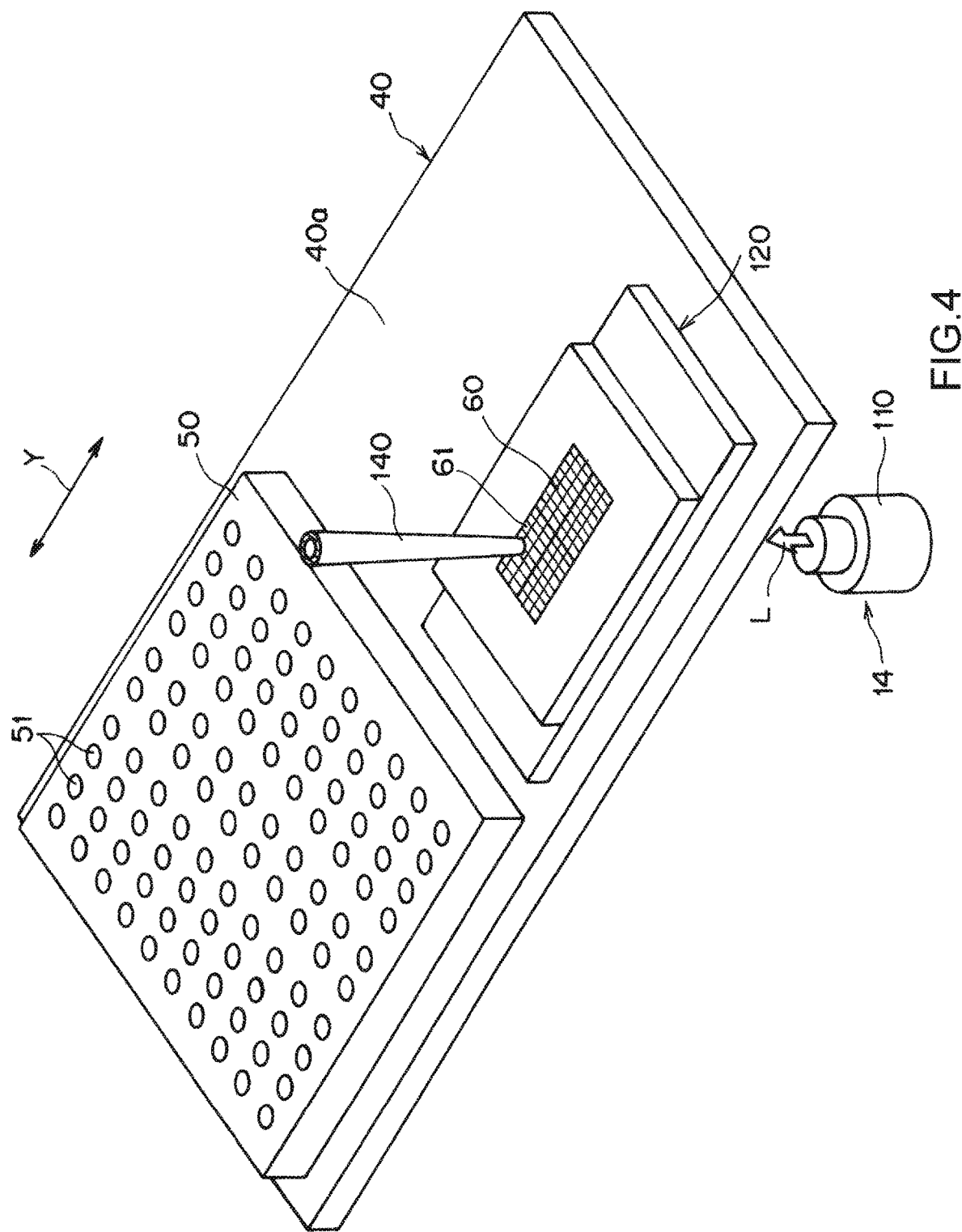
FIG. 4 is a perspective view illustrating a structure of the mounting table shown in FIG. 3.

FIG. 4 is a perspective view illustrating structures of the accommodating plate 50 and the cell accommodating chip 60 on the mounting table 40 shown in FIG. 3.

The mounting table 40 is, for example, a rectangular plate-like member, and the accommodating plate 50 and the cell accommodating chip 60 are detachably mounted on a mounting surface 40a of the mounting table 40 sequentially in the Y-direction.

The accommodating plate 50 is a plate-like member and is provided with a large number of wells 51 arranged at constant intervals along the X-direction and the Y-direction in a matrix form. These wells 51 form a collecting-and-storing section that can separately collect and store cells as target samples when the cells are sequentially ejected from a suction/discharge capillary 140. The wells 51 of the accommodating plate 50 are, for example, recessed portions having a substantially U-shaped vertical-direction cross section or recessed portions having a cup shape.

The cell accommodating chip 60 is secured on the mounting surface 40a of the mounting table 40 by a securing member 120, and the securing member 120 is positioned at and fixed to a predetermined position of the mounting table 40.

Figure 5:
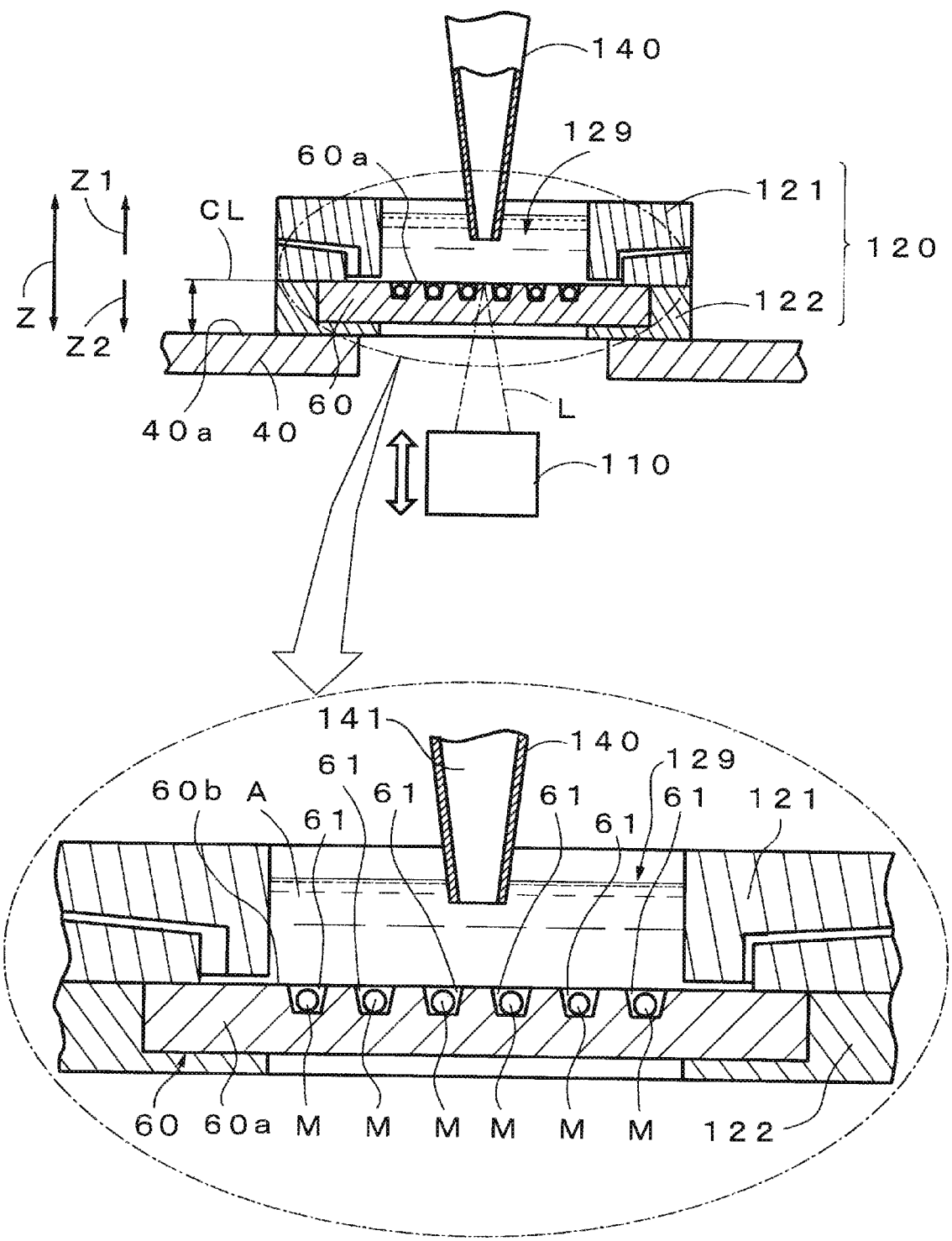
FIG. 5 is an enlarged cross-sectional view illustrating the structures of a cell accommodating chip and a securing member of the cell accommodating chip.

FIG. 5 is an enlarged cross-sectional view illustrating the structures of the cell accommodating chip 60 and the securing member 120. As shown in the drawing, the securing member 120 is structured such that the cell accommodating chip 60 can be secured and held at a position of a reference plane CL at a certain height with respect to the mounting surface 40a of the mounting table 40. Specifically, the securing member 120 includes frames 121 and 122 arranged so as to surround the edge of the cell accommodating chip 60 and holds the cell accommodating chip 60 in cooperation with these members.

The cell accommodating chip 60 is arranged between the frames 121 and 122 in the Z-direction and is sandwiched between the frames 121 and 122 so as to be in pressure contact with each of the frames 121 and 122. Consequently, the sealing property between the cell accommodating chip 60 and the frame 121 is ensured.

In the state in which the cell accommodating chip 60 is being in pressure contact with the frame 121, the upper surface 60b of the cell accommodating chip 60 is positioned at the reference plane CL via the frame 122. Consequently, it is possible to precisely control the distances in the Z-direction from the upper surface 60b of the cell accommodating chip 60 to the objective lens 110 of the measuring section 14 and to the accommodating plate 50. In other words, it possible to precisely control the position of a cell M in a well 61 of the cell accommodating chip 60 and the distance between the objective lens 110 of the measuring section 14 and the accommodating plate 50.

The frame 121 includes a liquid-holding section 129 disposed at the central part in the plane direction of the frame and above the cell accommodating chip 60 and holding a liquid A and is thereby structured so as to be capable of holding each type of liquid, such as a medium, a reagent solution, and a reaction solution. That is, the liquid-holding section 129 is formed in an internal space of the frame 121. The frame 121 is openable with respect to the frame 122 by using, for example, a hinge mechanism section (not shown in the drawing), which allows the cell accommodating chip 60 in the securing member 120 to be taken out and be replaced with a new cell accommodating chip. The cell accommodating chip 60 is a plate-like member capable of accommodating a plurality of cells M. Detailed structure of the cell accommodating chip 60 will be described below.

The collecting section 13 includes a suction/discharge capillary 140 for isolating the identified cell M as a target sample. The suction/discharge capillary 140 is a tapered hollow member whose diameter decreases along the Z2-direction (downward direction) and has a conduit 141 formed in the inside.

Returning to FIG. 1, the measuring section 14 irradiates a region including a plurality of wells 61 of the cell accommodating chip 60 with light L to generate fluorescence from a cell M and/or a well 61 accommodating a cell or in the vicinity thereof in the region, and receives the fluorescence. The fluorescence from the cell M and/or the well 61 accommodating a cell or in the vicinity thereof that received the light is subjected to image analysis by the image analyzing section 15.

Specifically, the measuring section 14 irradiates the cell accommodating chip 60 and cells M accommodated in the cell accommodating chip 60 with light guided from at least one light source and hence acquires shape and position information from transmitted light, reflected light, or fluorescence and brightness information, such as fluorescence and chemiluminescence, with a resolution finer than the average size of microparticles and also acquires information on, for example, the shape of the cell accommodating chip 60 itself and the positional coordinate and size of the wells 61 arranged on the cell accommodating chip 60.

The measuring section 14 includes an objective lens 110, and the objective lens 110 guides light to the cell accommodating chip 60. The objective lens 110 is arranged below the cell accommodating chip 60 and the moving section 16, and the suction/discharge capillary 140 is arranged above the cell accommodating chip 60 and the moving section 16. That is, the cell accommodating chip 60 and the moving section 16 are arranged between the objective lens 110 and the suction/discharge capillary 140 in the Z-direction.

The measuring section 14 includes an excitation light source 181 as a light source, an optical filter (excitation filter) 184 for selecting only a desired excitation wavelength band from light irradiated from the excitation light source 181, an optical filter (fluorescence filter) 185 for selecting only a desired wavelength band of optical information from the cell accommodating chip 60, a fluorescence filter unit 183 includes a dichroic mirror 186 for switching the optical path depending on the difference between the wavelength bands of the excitation light and the optical information, an objective lens 110 for guiding the light emitted from the excitation light source 181 to the cell accommodating chip 60 and collecting optical information obtained from the cell accommodating chip 60, a focus unit 187 having an automatic focus function capable of moving the objective lens 110 in the optical axis direction, and a light-receiving section 188 as a light-detecting section for detecting optical information from a measurement target. The fluorescence filter unit 183 and the light-receiving section 188 are fixed to an epifluorescence unit 190.

The excitation light source 181 includes, for example, a laser light source or a mercury lamp. A shutter unit 182 is arranged between the excitation light source 181 and the fluorescence filter unit 183 and it is possible that the shutter unit 182 blocks light L produced by the excitation light source 181 before reaching the fluorescence filter unit 183 when the shutter unit 182 does not irradiate the cell M on the cell accommodating chip 60 with light L.

Furthermore, the measuring section 14 includes a half mirror (not shown in the drawing), and by switching the half mirror and the fluorescence filter unit 183, irradiates an observation target with a part of the light from the excitation light source 181, and, at the same time, a part of the reflection light from the observation target is guided to the light-receiving section 188, which allows measurement of the shape and position information of the upper surface 60b of the cell accommodating chip 60 and the wells 61 formed on the upper surface.

In the measuring section 14, a plurality of objective lens 110a, 110b, . . . are rotated, for example, in a revolve manner, and thereby an objective lens of a required magnification can be positioned below the cell accommodating chip 60. The focus unit 187 can perform focus adjustment of the objective lens 110 on a microparticle M on the cell accommodating chip 60 by, for example, operating the motor 189 in response to a command from the control unit 100 and moving and positioning, for example, the objective lens 110, disposed below the cell accommodating chip 60, along the Z-direction.

The image analyzing section 15 calculates the fluorescent brightness of at least a cell M and/or a well 61 accommodating a cell or in the vicinity thereof emitting fluorescence of a maximum intensity among a plurality of cells M in the respective wells 61 and/or the wells 61 accommodating cells or in the vicinities thereof.

Specifically, the image analyzing section 15 acquires at least data for verifying the presence of a cell M satisfying a brightness condition, which can be set by an observer, in each well 61 by analyzing the measured shape information and optical information. The image analyzing section 15 extracts optical information from a cell M and/or a well 61 accommodating a cell or in the vicinity thereof by matching the positional coordinate information of the well 61 by transmitted light or reflected light and the optical information of fluorescence/chemiluminescence. The measuring section 14 has an automatic focus function and is capable of performing measurement while being focused at a predetermined position and capable of determining a positional relationship between the distal end of the suction/discharge capillary 140 and the upper surface of the cell accommodating chip 60 by automatically focusing on both of them.

The control unit 100 detects, in an X-Y plane, the position of a well 61 emitting fluorescence having a brightness satisfying a collecting condition. The control unit 100 is capable of positioning a well 61 of the cell accommodating chip 60 on the moving section 16 directly below the suction/discharge capillary 140 by sending a control driving signal to the motors 164 and 169 shown in FIG. 3. That is, the suction/discharge capillary 140 is configured so as to be capable of targeting a specific cell to suck the cell in the well. In addition, the suction/discharge capillary 140 is capable of sucking a single or a plurality of cells from a well selected from a plurality of wells, i.e., a well accommodating a cell satisfying a predetermined collecting condition. Furthermore, the suction/discharge capillary 140 is capable of discharging the sucked single or plurality of cells into a predetermined well 51 of the accommodating plate 50.

(Structure of Cell Accommodating Chip)

Figure 6:
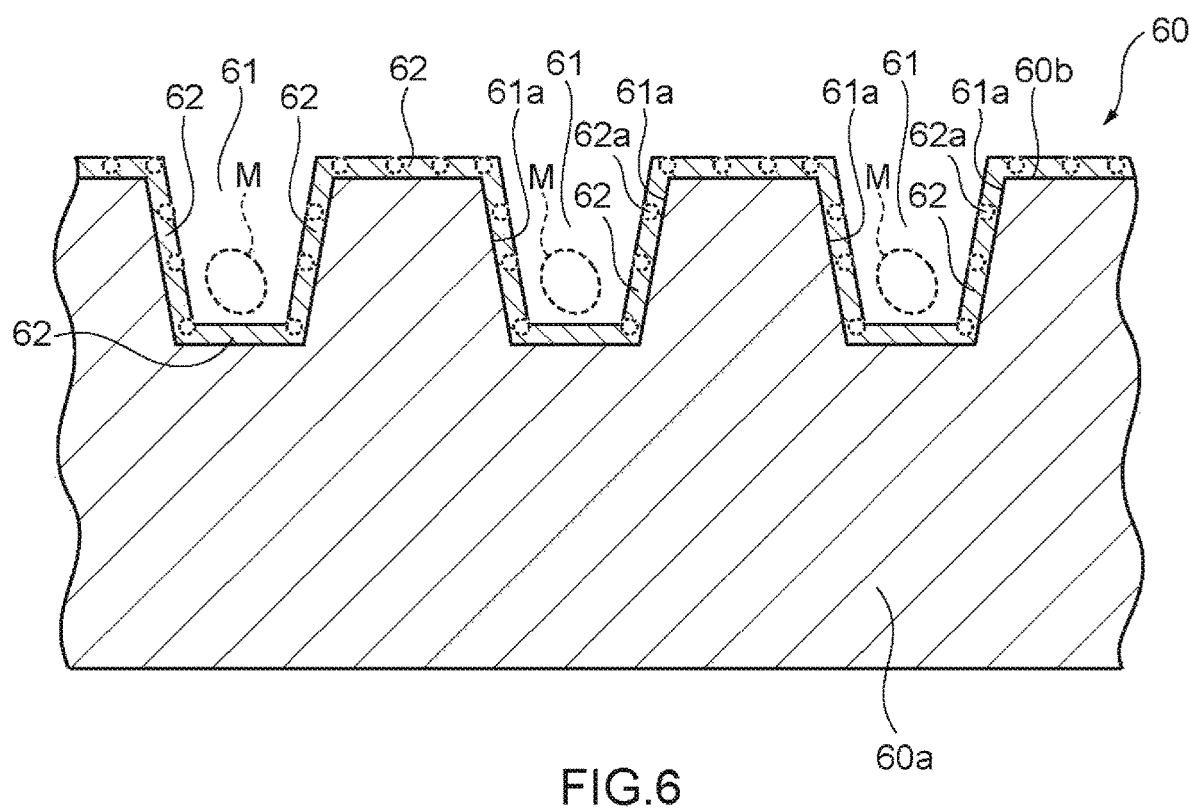
FIG. 6 is a partial cross-sectional view illustrating the detailed structure of the cell accommodating chip shown in FIG. 5.

FIG. 6 is a partial cross-sectional view illustrating the detailed structure of the cell accommodating chip 60 shown in FIG. 5. As shown in the drawing, the cell accommodating chip 60 includes a substrate 60a composed of a light-transmitting material and a plurality of wells 61, 61, . . . , disposed on the upper surface 60b (at least one of main faces) of the substrate and capable of accommodating a plurality of cells M on one-to-one basis.

By means of this surface shape of the cell accommodating chip 60 and modification of the surface by a dry process, the surface of the cell accommodating chip may be configured so as not to have the coating layer, but a case in which a coating layer is formed will now be described in detail.

The cell accommodating chip 60 includes a coating layer 62 formed on the inner surface 61a of each well constituting the plurality of wells 61, 61, . . . , and on the upper surface 60b of the substrate 60a. The coating layer 62 may be formed on only the inner surface 61a of the well 61 or may be formed on both the inner surface 61a of the well 61 and the upper surface 60b of the substrate 60a.

The cell accommodating chip 60 is composed of, for example, glass, plastic, or a material containing any of them as a main component, and a large number of wells 61 are arranged in, for example, a matrix form on the upper surface 60b. Each well 61 is a recessed portion having a vertical cross section of a substantially trapezoidal shape or a recessed portion having a substantially cup shape, and a horizontal cross-sectional shape of the well 61 is preferably substantially circular. The well 61 has a size corresponding to the accommodation of a single cell M when cells M are dispensed or collectively injected on the cell accommodating chip 60. For example, when the horizontal cross-sectional shape of the well 61 is a circle, the inner diameter and the depth of the well are each preferably slightly greater than the diameter of a cell, e.g., about 20 μm for a cell M having a diameter of 15 μm. It is preferable that the well 61 has a size corresponding to a single cell M and is more preferable that it has a size allowing only a single cell M to enter.

The surface of the coating layer 62 has a low cell adhesion property to cells and has affinity to a specific binding material that has affinity to a produced substance produced by a cell M accommodated in a well 61 and/or a released substance released by a cell M accommodated in a well 61.

Specifically, the coating layer 62 includes, for example, a binding material that binds to a specific binding material having affinity to a produced substance produced by a cell M accommodated in a well 61 or a released substance released by a cell M accommodated in a well 61 and a low cell adhesive material having low adhesion to the cell M in the well 61.

Furthermore, it is preferable that the surface of the coating layer 62 have hydrophilicity, a low cell adhesion property, and affinity to a specific binding material having affinity to a produced substance produced by a cell M accommodated in a well 61 and/or a released substance released by a cell M accommodated in a well 61. Specifically, the coating layer 62 may include, for example, a hydrophilic material, a low cell adhesive material having low adhesion to a cell M in the well 61, and a binding material that binds to a specific binding material having affinity to a produced substance produced by the cell M accommodated in the well 61 and/or a released substance released by the cell M accommodated in the well 61. Alternatively, in the coating layer 62, the low cell adhesive material having low adhesion to a cell M in a well 61 or the binding material that binds to a specific binding material having affinity to a produced substance produced by the cell M accommodated in the well 61 and/or a released substance released by the cell M accommodated in the well 61 may have hydrophilicity.

It is preferable that the binding material be a functional group-containing material having at least one of functional groups described below or at least one selected from streptavidin, avidin, biotin, and derivatives thereof. Consequently, the binding material on the surface of the coating layer 62 binds to a specific binding material that binds to a produced substance produced by the cell accommodated in the well 61 or a released substance released by the cell accommodated in the well 61, and the specific binding material binds to the produced substance and/or the released substance.

The low cell adhesive material constitutes a main component of the coating layer 62, and the binding material that binds to the specific binding material is uniformly distributed in the coating layer 62 in the in-plane direction of the coating layer 62. The low cell adhesive material is preferably, for example, a material having low protein adsorption to proteins. The hydrophilic material may constitute a main component of the coating layer 62 together with the low cell adhesive material or may be uniformly distributed in the coating layer 62 in the in-plane direction of the coating layer 62 together with the binding material that binds to the specific binding material.

The hydrophilic material the binding material, and the low cell adhesive material contained in the coating layer 62 can be constituted in following combinations. The case where the binding material is a functional group-containing material will now be described as an example.

As shown in FIG. 7A, an exemplary configuration may have a material having both hydrophilicity and a low cell adhesion property as a first material and a functional group-containing material as a second material. The first material may constitute a main component of the coating layer 62.

Further, as shown in FIG. 7B, an exemplary configuration may have a material having both hydrophilicity and a low cell adhesion property as a first material and a functional group-containing material having hydrophilicity as a second material, and as shown in FIG. 7C, an exemplary configuration may have a material having a low cell adhesion property as a first material and a functional group-containing material having hydrophilicity as a second material, and as shown in FIG. 7D, an exemplary configuration may have a material having a low cell adhesion property as a first material, a material having hydrophilicity as a second material, and a functional group-containing material as a third material.

Further, as shown in FIG. 7E, an exemplary configuration may have a material having a low cell adhesion property as a first material and a functional group-containing material as a second material.

The hydrophilic material is a material having good wettability to a liquid containing cells M. As a standard for the good wettability, it is preferable that the contact angle between distilled water and the coating layer 62 be 60° or less.

It is preferable that the functional group-containing material have at least one functional group selected from an active ester group, an amino group, a carboxyl group, a thiol group, an aldehyde group, a hydrazino group, a hydroxylamino group, and a bromoacetyl group. Consequently, the functional group is chemically bound to the specific binding material, which allows the produced substance and/or the released substance to favorably bind to the coating layer 62 in the well 61.

When the binding material is streptavidin, avidin, biotin, or a derivative thereof, the binding is achieved by affinity due to a chemical or physical factor other than covalent bonds.

(Method of Using Cell Accommodating Chip)

Figure 8:
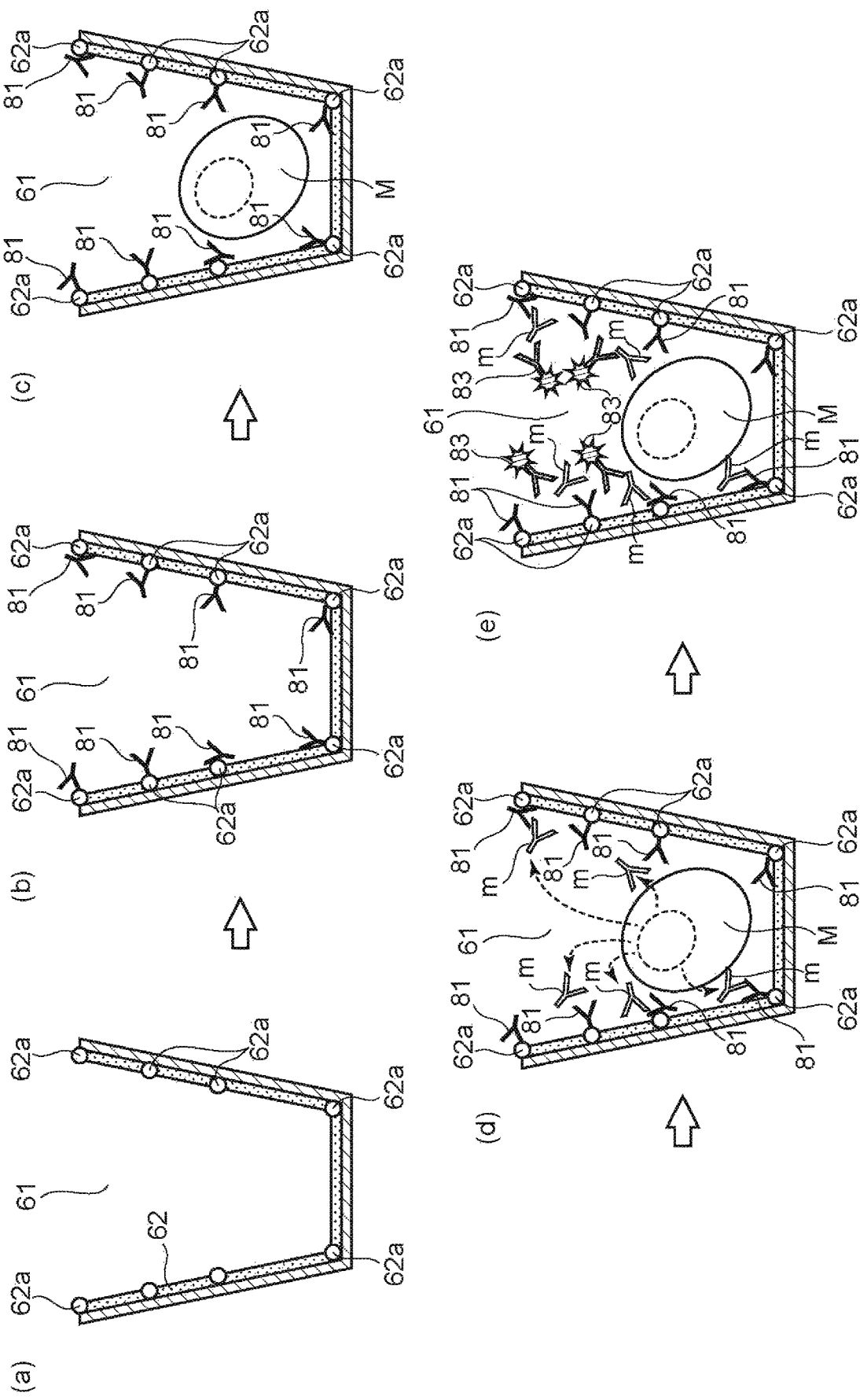
FIG. 8 is a diagram including schematic views (a) to (e) for explaining a method for using the cell accommodating chip shown in FIG. 6.

FIG. 8 is a diagram including schematic views (a) to (e) for explaining a method for using the cell accommodating chip 60 structured as described above.

First of all, in the coating layer 62 formed on the inner surface 61a of a well 61 (FIG. 8(a)), a predetermined functional group 62a, for example, an active ester group, of a functional group-containing material contained in the coating layer is bound to a specific binding material 81, such as a primary antibody (FIG. 8(b)). Here, a coupling solution containing the specific binding material 81 that binds the predetermined functional group 62a and a produced substance m that is produced by a cell M to be accommodated in the well 61 is used, and the coupling solution is introduced on the cell accommodating chip 60. Consequently, the predetermined functional group 62a and the specific binding material 81 are bound to each other.

In the case where PEG or its derivative is used as the low protein adsorption material, the coupling solution is preferably alkaline and, specifically, preferably has a pH of 7 to 10. By using such a coupling solution, a natural state due to buffer action can be maintained, the specific binding material 81 (e.g., a protein) is prevented from being damaged by denaturation or the like, and good binding between the predetermined functional group 62a and the produced substance m can be obtained.

The specific binding material 81 is a binding substance that specifically binds to the produced substance. The specific binding material 81 is not limited to a primary antibody and may be an antigen or a substance other than protein. The specific binding material 81 used in the present disclosure is, for example, a chemical material such as a protein including cytokine, an immunoglobulin, an anti-immunoglobulin, and a hormone; or a chelating agent. Alternatively, a binding material capable of binding to the produced substance by a cell accommodated in a well 61 may be used instead of the specific binding material 81.

Subsequently, after washing the inside of the well 61, an incubation medium containing a cell M is accommodated in the well 61, the cell M is incubated in the well 61 (FIG. 8(c)). The cell M generates a produced substance m, such as a produced antibody, by the incubation, and the produced substance m binds to the specific binding material 81 in the well 61 (FIG. 8(d)). As a result, the predetermined functional group 62a binds to the produced substance m via the specific binding material 81. The present disclosure can be applied to the identification of all cell types. The cell types are, for example, immune cell lines, such as B cells, T cells, and dendritic cells; cancer cell lines, such as CTC cells; stem cell lines, such as iPS cells and ES cells; hybridomas; CHO cells; and yeast cells. The produced substance is a protein, such as cytokine, an immunoglobulin, an anti-immunoglobulin, or a hormone; or a chemical material, such as a vitamin. Furthermore, instead of the produced substance m, a released substance, which is a metal ion such as a calcium ion, released by a cell may be used.

After washing the inside of the well 61, an optical information-holding substance 83, such as a fluorescent molecule (e.g., fluorescence-attached secondary antibody), specifically binding to the produced substance m or the specific binding material 81 is bound thereto (FIG. 8(e)). Thus, the produced substance m produced by the cell M is bound to the specific binding material 81 bound onto the coating layer 62 in the well 61 accommodating the cell M; the optical information-holding substance 83 is bound to the produced substance m or the specific binding material 81; and the optical information of the optical information-holding substance 83 is detected. Consequently, it is possible to precisely identify a target sample using the well 61 as a marker, while maintaining the cell M and the produced substance m in the well 61 in a wet state.

(Screening Method)

The screening apparatus 1 structured as described above collects a target sample using the above-described cell accommodating chip 60 as follows.

Figure 9:
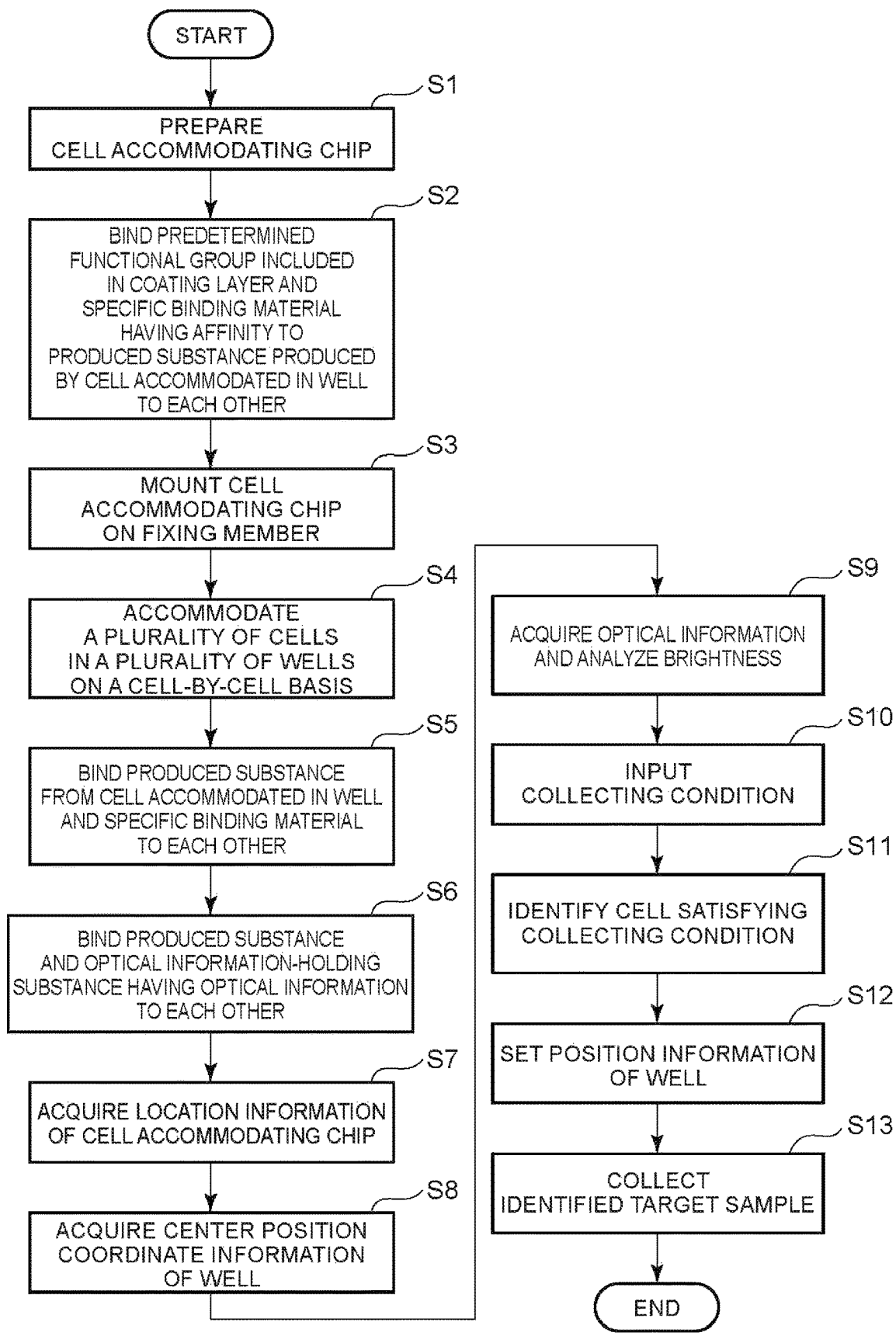
FIG. 9 is a flow chart illustrating a screening method using the cell accommodating chip shown in FIG. 8.

FIG. 9 is a flow chart illustrating a screening method using the cell accommodating chip 60 shown in FIG. 8, and FIGS. 10A to 10D are schematic views for explaining each step of FIG. 9.

Figure 10A:
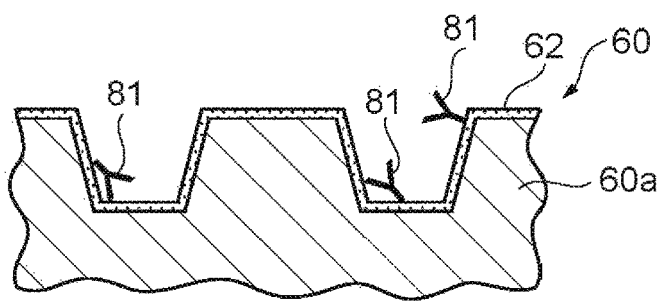
FIGS. 10A to 10D are schematic views for explaining each step of FIG. 9.

As shown in FIG. 9, a cell accommodating chip 60 configured as described above is prepared (Step S1), and a predetermined functional group 62a (see FIG. 8) contained in the coating layer 62 and a specific binding material 81 (binding material) having affinity to a produced substance m produced by the cell accommodated in a well 61 are bound to each other (Step S2) (FIG. 10A). For example, a coupling solution containing a primary antibody is added dropwise or applied onto the coating layer 62 in the wells 61 to bind the primary antibody thereto.

Subsequently, the top of the cell accommodating chip 60 and the insides of the wells 61 are washed to remove the specific binding material not bound to the coating layer 62. After the washing, the cell accommodating chip 60 is mounted on the securing member 120 of the screening apparatus 1 (Step S3). Step S3 may be performed between Step S1 and Step S2.

Figure 10B:
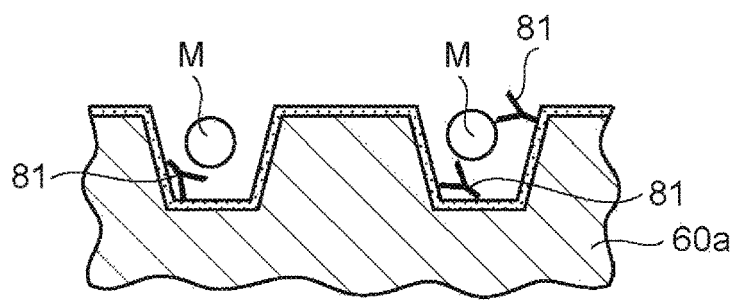

Subsequently, a liquid (e.g., incubation medium) containing a plurality of cells M is introduced to the wells 61 on the cell accommodating chip 60 to accommodate the plurality of cells M in the plurality of wells 61 on a cell basis (Step S4) (FIG. 10B). The introduced liquid is left to stand for a predetermined period of time for waiting that each cell precipitates and enters into each well one by one. The cells M not accommodated in the wells 61 are removed by washing.

Figure 10C:
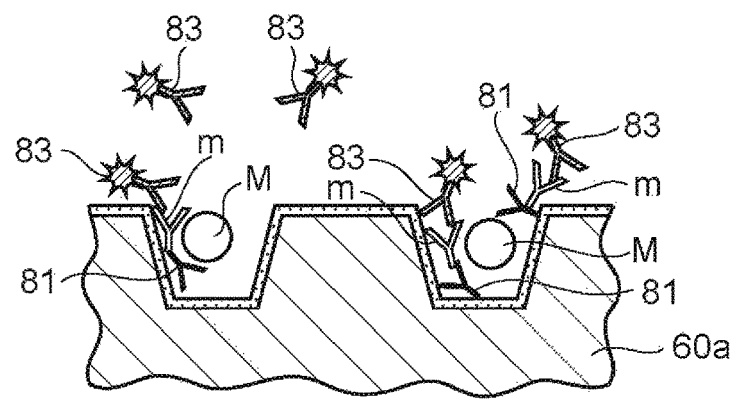

After the washing, the cell M accommodated in the well 61 is incubated to stimulate the production of a produced substance m, and the produced substance m produced by the cell M and the specific binding material 81 are bound to each other (Step S5). The cell incubation conditions (e.g., temperature, type of gas, and concentration) can be selected depending on the cell type, a purpose, etc. The incubation time of the cell M accommodated in the well 61 can be changed as needed. Subsequently, the produced substance m and the optical information-holding substance 83 having optical information, such as a fluorescent molecule, specifically binding to the produced substance m are bound to each other (Step S6) (FIG. 10C). The produced substance m or the specific binding material 81, and an optical information-holding substance 83 specifically binding thereto and having optical information, such as a fluorescent molecule, may be bound to each other. For example, a solution containing a fluorescence-attached secondary antibody is added dropwise onto the cell accommodating chip 60, and this fluorescence-attached secondary antibody and the produced substance m are bound to each other. The optical information-holding substance 83 may be a functional group-attached fluorescent dye, a biotinated antibody+avidinated fluorescent dye, a fluorescent bead-attached secondary antibody, or the like, in addition to the fluorescence-attached secondary antibody. The treatment of Step S6 may be performed simultaneously with the treatment of Step S5. Subsequently, the top of the cell accommodating chip 60 and the insides of the wells 61 are washed, and the optical information-holding substance 83 not bound to the produced substance m or the specific binding material 81 is removed.

Subsequently, for example, information on the reference position of the cell accommodating chip or a correction parameter is acquired as location information of the cell accommodating chip 60 (Step S7), and the center position coordinate information of each well is acquired by image analysis (Step S8).

Subsequently, the cell accommodating chip 60 is irradiated with light, and the optical information of the optical information-holding substance 83 is acquired and is subjected to brightness analysis (Step S9). The optical information of the optical information-holding substance 83 fluorescent based on the photoirradiation in Step S9 may be acquired, or the optical information of the previously fluorescent optical information-holding substance 83 may be acquired. As the brightness analysis, a change with time of the fluorescent information obtained from the optical information-holding substance 83 may be measured.

Subsequently, based on the acquired brightness information, a collecting condition of microparticles desired by a user may be, for example, the brightness of a fluorescence is higher than a predetermined threshold value, or the brightness of at least one of the fluorescences is higher than a predetermined threshold value in the case a plurality of fluorescence (e.g., different fluorescent colors) are used, or any combination thereof. In addition, the brightness of any fluorescence may be combined with those excluded from the collection (those lower than a threshold value). Some conditions determined as described above are input (Step S10), and the cell M is identified as a target sample based on the collecting condition (Step S11). For example, the cell M accommodated in the well 61 emitting light with brightness satisfying the above-mentioned collecting condition is identified as a target sample.

Figure 10D:
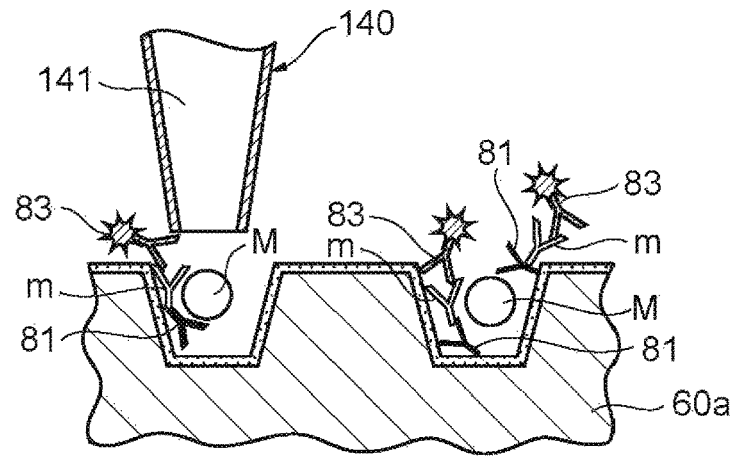

Subsequently, the center position of the suction/discharge capillary 140 is acquired by, for example, image analysis, and the center position or a position shifted from the center position by a predetermined distance is set as the center position (position information) of each well in the cell collection (Step S12). The center position of the well 61 accommodating the target sample is moved so as to fit the center position of the well set in Step S12, and target samples identified in Step S11 are sequentially collected (Step S13) (FIG. 10D). The collected target samples are accommodated in predetermined wells 51 on the accommodating plate 50 set by the user in advance.

(Evaluation of Hydrophilicity of Cell Accommodating Chip)

Figure 11:
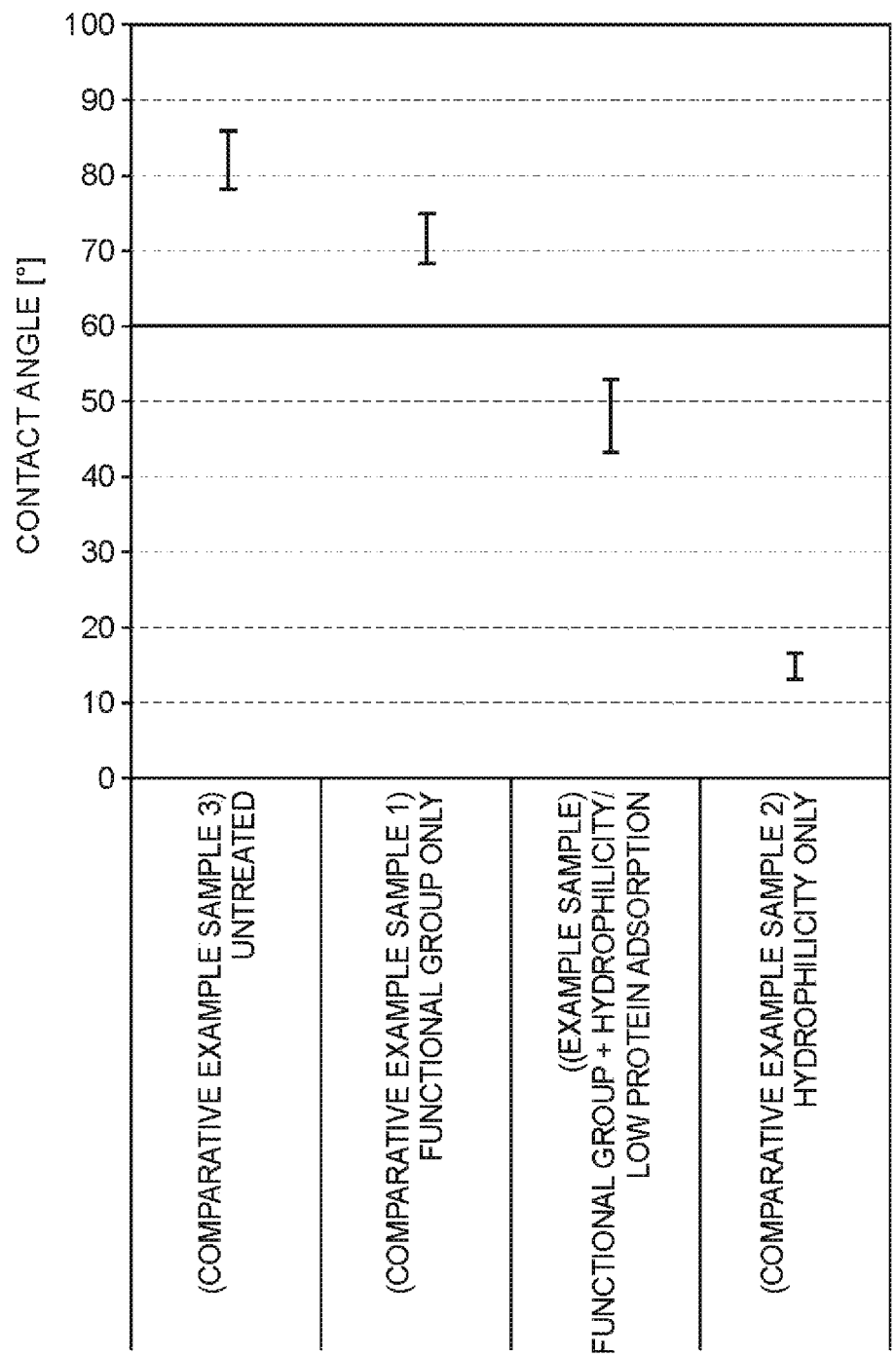
FIG. 11 is a graph showing the results in measurement and comparison of contact angles between a variety of cell accommodating chips and distilled water.

FIG. 11 is a graph showing the results in measurement and comparison of contact angles between a variety of cell accommodating chips and distilled water.

In the present evaluation, as an Inventive Example Sample, a coating layer containing a first material having both hydrophilicity and low protein adsorption, and a second material which is a functional group-containing material (see FIG. 7A) was used. Specifically, a PEG derivative was used as a first material, and a material having an active ester group was used as a second material. As a Comparative Example Sample 1, a coating layer containing only a functional group-containing material was used; as a Comparative Example Sample 2, a coating layer containing only a hydrophilic material was used; and as a Comparative Example Sample 3, an untreated cell accommodating chip that does not have a coating layer was used. In all samples, the material and shape of the substrates and the method for producing the substrates were the same.

The contact angle was measured in accordance with JIS R3257 and the contact angle was calculated by a static method as shown below. The contact angle θ (°) was determined from the radius r (mm) and the height h (mm) when 1 μL of distilled water was dropped onto a cell accommodating chip. Here, the radius r is a radius of the surface of the water drop in contact with the chip surface, and the height h is a height from the chip surface to the top of the water drop. The average value when 6 points were measured per sample was calculated.

As shown in FIG. 11, when the coating layer contains a functional group-containing material only (Comparative Example Sample 1), the contact angle between the coating layer and distilled water is 69° to 75°, and the average value is 72°. In contrast, the coating layer of the present disclosure (Example Sample) contains a material having both hydrophilicity and low protein adsorption and a functional group-containing material, and the contact angle is 44° to 53°, an average value is 50°, and it is demonstrated that the hydrophilicity has been considerably improved. When the coating layer contains a hydrophilic material only (Comparative Example Sample 2), the contact angle between the cell accommodating chip and a liquid containing cells is 14° to 17°, an average value is 15°, it is difficult to bind a specific binding material having affinity to a produced substance, and the cell accommodated in the well and proteins such as the produced substance could adsorb to the coating layer. In the case of an untreated cell accommodating chip (Comparative Example Sample 3), the contact angle is 78° to 86°, an average value is 83°, and the wettability is obviously low. These measurement results demonstrate that the coating layer of the present embodiment is capable of suppressing adsorption of proteins and achieving satisfactory hydrophilicity while allowing the binding of the specific binding material having affinity to the produced substance.

(Evaluation of Hydrophilicity Based on Bubble Ratio of Well)

Since the wells formed in the cell accommodating chip are minute, the hydrophilicity of the cell accommodating chip containing the wells highly affects the inflow of a liquid containing cells into the wells. Accordingly, in order to verify and evaluate the influence of the contact angle of the cell accommodating chip on the bubble ratio occurring in the wells, which is an index of hydrophilicity, the following test was performed.

First of all, each of the cell accommodating chips was set in a securing member, PBS (phosphate buffered saline) of ordinary temperature was introduced on the cell accommodating chip, and the proportion of the number of wells having bubbles therein in random 500 wells on the chip was determined as a bubble ratio. The bubble ratios were determined at immediately after introduction of the buffer (bubble ratio (1)), after an elapse of time t (t=5 minutes) after introduction of the buffer (bubble ratio (2)), and after an elapse of time 2t (10 minutes) after introduction of the buffer (bubble ratio (3)). In the present evaluation, the same Example Sample and Comparative Example Samples as those in the evaluation of hydrophilicity were used. The results are shown in Table 1.

TABLE 1

|  | Contact angle (average value) | Bubble ratio (1) | Bubble ratio (2) | Bubble ratio (3) |
| --- | --- | --- | --- | --- |
| Example Sample | 50° | 98% | 7% | 0% |
| Comparative Example Sample 1 | 72° | 100% | 100% | 96% |
| Comparative Example Sample 2 | 15° | 0% | 0% | 0% |
| Comparative Example Sample 3 | 83° | 100% | 100% | 100% |

It is demonstrated from the results of Table 1 that in the case of the coating layer of the present embodiment (Example Sample), the bubble ratios (1) to (3) of the wells were 98%, 7%, and 0%, respectively, although bubbles were found in a large number of wells immediately after introduction of PBS, the bubbles promptly escaped, and the bubbles escaped from almost all wells after an elapse of a certain time. In contrast, in the case of the coating layer containing the functional group-containing material only (Comparative Example Sample 1), the bubble ratios (1) to (3) of the wells were 100%, 100%, and 96%, respectively, bubbles were formed in almost all wells immediately after introduction of PBS, and the bubbles remained in almost all wells even after an elapse of a predetermined time. In addition, in the case of a coating layer containing a hydrophilic material only (Comparative Example Sample 2), the bubble ratios (1) to (3) of the wells were all 0%, wells having bubbles were not found immediately after introduction of PBS and also after an elapse of a predetermined time. In the case of the untreated cell accommodating chip (Comparative Example Sample 3), the bubble ratios (1) to (3) of the wells were all 100%, bubbles were formed in all wells immediately after introduction of PBS, and the bubbles remained in all wells even after an elapse of a predetermined time.

When accommodating cells in the wells, a liquid containing the cells (also referred to as cell suspension) is introduced on the cell accommodating chip and is left to stand, and the cells then slowly precipitate in the liquid and are accommodated in the wells. However, if the wettability of the surface of the cell accommodating chip and the surface of the well is low, bubbles are produced in the well, the progress of precipitation of the cell is prevented by the bubbles in the well, and it is impossible to accommodate the cell in the well. Accordingly, the surface of the cell accommodating chip needs to have hydrophilicity that allows bubbles in the well to escape before the cell precipitates in the liquid. According to the present embodiment, it was confirmed that if the contact angle of the surface of the cell accommodating chip is 60° or less, the surface of the cell accommodating chip has the sufficient hydrophilicity for suppressing the retention of bubbles in the well, and a cell can be positively accommodated in the fine well.

(Evaluation of Low Cell Adhesion Property of Cell Accommodating Chip)

Subsequently, the adhesion rates of cells to the coating layers similar to the samples used in the evaluation shown in FIG. 11 were measured and compared.

The measurement and evaluation of the adhesion rates of cells were performed as follows. As shown in FIG. 9, firstly, a primary antibody-containing coupling solution was added dropwise onto each of the cell accommodating chips to bind the primary antibody. Subsequently, the surface of the cell accommodating chip was washed to remove the unbound primary antibody and the components of the coupling solution. After the washing, each of the cell accommodating chips was set to the securing member, an incubation medium containing a plurality of 293T cells was introduced on the cell accommodating chip, and the plurality of cells were accommodated in a plurality of wells on a cell basis. Subsequently, the cells not accommodated in the wells were removed by washing. After the washing, the cell accommodating chip and the cells accommodated in the wells are incubated for 60 minutes, and when the 48 cells stored in the wells on the cell accommodating chip were tried to be collected with a cell-screening apparatus including a collection mechanism, the proportion of the cells that adhered to the surface of the cell accommodating drip and could not be collected was defined as the adhesion rate. The measurement points were n=48.

In the present evaluation, the same Example Sample and Comparative Example Samples 1 and 2 as those in aforementioned evaluation of hydrophilicity were used. The results are shown in Table 2.

TABLE 2

| | Cell type | Contact angle (average value) | Adhesion rate |
|---|---|---|---|
| Example Sample | 293T | 50° | 4% |
| Comparative Example Sample 1 | 293T | 72° | 96% |
| Comparative Example Sample 2 | 293T | 15° | 83% |

As shown in Table 2, it is demonstrated that in the case of the coating layer of the present embodiment (Example Sample), the adhesion rate of 293T cells was about 4% (two cells), and most of the 293T cells did not adhere to the coating layer. In contrast, it is demonstrated that in the case of the coating layer containing the functional group-containing material only (Comparative Example Sample 1), the adhesion rate of the 293T cells was about 96% (46 cells), and most of the cells adhered to the coating layer. It is also demonstrated that in the case of the coating layer containing the hydrophilic material only (Comparative Example Sample 2), the adhesion rate was about 83% (40 cells), and most of the cells adhered to the coating layer. The results demonstrated that according to the coating layer of the present embodiment, the adhesion rate of cells to the coating layer is remarkably low, the coating layer in a well hardly adheres to the cell accommodated in the well, and favorable a low cell adhesion property can be achieved.

As described above, according to the present embodiment, the surface of the coating layer 62 in a plurality of wells 61 has a low cell adhesion property and has affinity to the specific binding material 81 having affinity to the produced substance m produced by the cell M accommodated in the well 61. The liquid containing cells M can easily enter fine wells 61 by means of the hydrophilic material of the coating layer 62, the accuracy of accommodating a single cell in each well can be enhanced, and the accuracy and efficiency of identifying and isolating a target sample can be improved. In addition, since chips of the related art have a structure in which a substance (e.g., Ig antibody) having affinity to the produced substance is bound on a chip in advance, it is difficult to store the chip for a long time, and accuracy may decrease due to drying or the like. In contrast, according to the present embodiment, the surface of the coating layer 62 has affinity to the specific binding material 81, and thereby there is no need to bind the specific binding material 81 having affinity to the produced substance m on the cell accommodating chip 60 in advance, and the reduction in accuracy due to drying or the like can be prevented. In addition, since the inside of the well 61 is hardly dried by the hydrophilicity of the coating layer 62 compared to the one of the related art, the inside of the well 61 can be kept wet even after binding of the specific binding material 81, and a reduction in accuracy due to drying or the like of the specific binding material 81 can be prevented. In addition, the specific binding material 81 binds to the predetermined functional group 62a by the affinity of the surface of the coating layer 62 to the specific binding material 81, and the produced substance m produced by the cell M in the well 61 of the coating layer 62 binds to the specific binding material 81. Accordingly, the well 61 itself can be used as a labeling site in identification of a target sample, and the target sample can be identified without damaging the cell M. Furthermore, since the surface of the coating layer 62 has a low cell adhesion property, the cell M in the well 61 can be prevented from adhering to the inner surface of the well and the upper surface 60b of the substrate 60a, the cell M as a target sample can be collected at high efficiency without requiring coating treatment using a blocking reagent or the like, and when collecting cells, the cell M can be collected without being damaged. In addition, since the coating layer 62 contains a low protein adsorption material, when the produced substance m is a protein, nonspecific adsorption of the produced substance m to the surface of the cell accommodating chip is prevented, and good detection sensitivity can be maintained without requiring coating treatment using a blocking reagent or the like.

In addition, according to the present embodiment, a cell accommodating chip 60 including a coating layer 62 having a surface that has a low cell adhesion property and affinity to a specific binding material 81 having affinity to a produced substance m produced by a cell M accommodated in a well 61 is prepared; and a specific binding material 81 is bound to the surface of the coating layer 62, a liquid containing a plurality of cells M is introduced to the cell accommodating chip 60 to accommodate the plurality of cells M in a plurality of wells 61 on a cell basis to bind the produced substance m from the cell M accommodated in the well 61 to the specific binding material 81, which allows the produced substance m or the specific binding material 81 to bind an optical information-holding substance 83 having optical information. It is therefore possible to identify and isolate the target sample with high accuracy and high efficiency. In addition, with simple handling, easy collection without damaging cells M in cell collection can be achieved.

A cell accommodating chip, a screening apparatus, and a screening method according to the present embodiment have been described above. However, the present disclosure is not limited to the above-described embodiments and can be variously modified and altered based on the technical idea of the present disclosure.

For example, in FIGS. 9 and 10A to 10D, the cell M accommodated in a well 61 emitting light with brightness satisfying the collecting condition is identified as a target sample (Step S11). That is, in FIGS. 9 and 10A to 10D, an optical information-holding substance 83 that specifically binds to the produced substance m (white Y in FIGS. 10A to 10D) that is secreted from the cell M is used, and the produced substance m produced by the cell M binds to the well 61 in which the cell M is accommodated. Accordingly, as described above, the timing of binding the optical information-holding substance 83 to the specific binding material 81 (Step S6) can be after Step S5 or simultaneous with Step S5.

In contrast, a screening method for identifying, as a target sample, the cell M accommodated in a well 61 other than the wells emitting light with brightness not lower than the threshold used in the above-described collecting condition may be used. Hereinafter, description of the same parts as those in the flow chart shown in FIG. 9 will be omitted, and different parts will be described.

Figure 12:
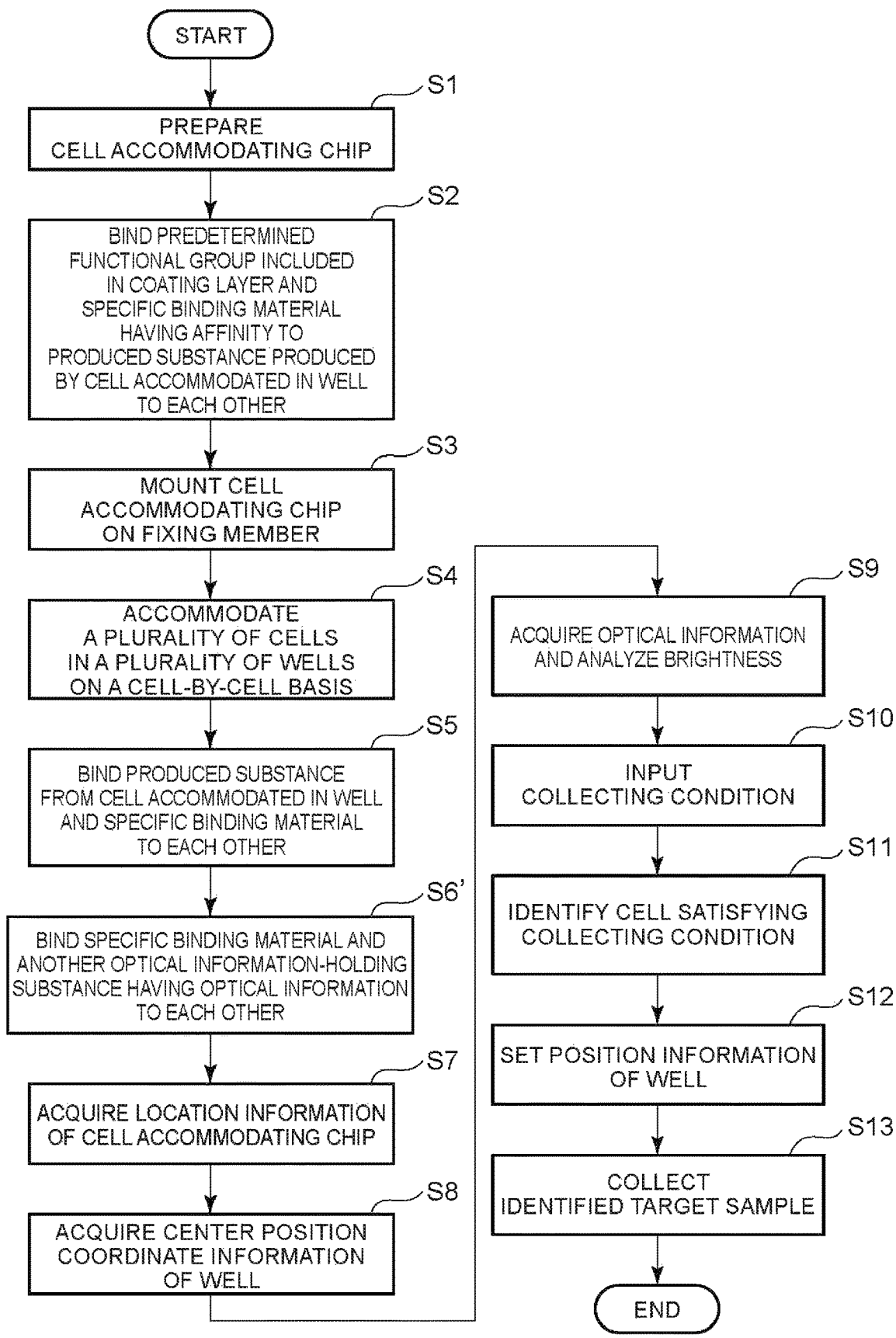
FIG. 12 is a flow chart illustrating a modified example of the screening method shown in FIG. 9.

As shown in FIG. 12, first of all, a plurality of cells M is accommodated in a plurality of wells 61 on a cell-by-cell basis (Step S4), and then each cell is incubated to stimulate the production of a produced substance m to bind the produced substance m produced by the cell M to the specific binding material 81 in the well 61 (Step S5). Consequently, the specific binding material 81 in the well 61 accommodating the cell M as a target sample is covered with the produced substance m, and the specific binding material 81 in the well 61 not accommodating the cell M as a target sample is not covered with the produced substance m. In this modification example, another optical information-holding substance not specifically binding to the produced substance m but specifically binding to the specific binding material 81 is used, and the another optical information-holding substance is bound to the specific binding material 81 (Step S6'). Consequently, the well 61 accommodating a cell M producing the produced substance m does not emit light, and the well 61 accommodating a cell M not producing the produced substance m emits light. Accordingly, in this method, Step S5 and Step S6' are not simultaneously performed, and Step S6' is performed after Step S5.

Subsequently, the optical information of the optical information-holding substance 83 is acquired and is subjected to brightness analysis (Step S9). Based on the acquired brightness information, a collecting condition of microparticles desired by a user is input (Step S10), and based on the collecting condition, a cell M is identified as a target sample (Step S11). The collecting condition is that light is not emitted or that the brightness is not higher than a predetermined threshold, and the cell M accommodated in a well 61 satisfying the collecting condition is identified as a target sample. By this method also, it is possible to collect a desired target sample.

What is claimed is:

1. A cell accommodating chip capable of accommodating a plurality of cells, comprising:
   a substrate composed of a light-transmitting material; and
   a plurality of wells on at least one of main faces of the substrate, the plurality of wells being capable of accommodating cells,
   a surface of the cell accommodating chip including the plurality of wells having:
   a low cell adhesion property;
   affinity to a specific binding material having affinity to a produced substance produced by a cell accommodated in one of the wells and/or a released substance released by the cell,
   a coating layer on the substrate, wherein
   the coating layer has a low cell adhesion property and affinity to the specific binding material having affinity to a generated substance generated by a cell accommodated in any of the wells and/or a released substance released by the cell, and
   the coating layer having affinity to the specific binding material is a coating layer including a binding material having affinity to the specific binding material, and
   the binding material is a functional group-containing material having at least one functional group selected from an active ester group, a carboxyl group, a thiol group, an aldehyde group, a hydrazino group, a hydroxylamino group, and a bromoacetyl group, or the binding material is at least one selected from streptavidin, avidin, biotin, and derivatives thereof, and
   wherein a contact angle of the surface having the coating layer of the cell accommodating chip is less than or equal to 60°,
   wherein the coating layer is formed on the inner surface of each of the wells and at least the main face with the wells of the substrate, and each of the wells has a size corresponding to accommodation of a single cell, and wherein the binding material is not bound to the specific binding material.

2. The cell accommodating chip according to claim 1, wherein the surface of the cell accommodating chip further has hydrophilicity.

3. The cell accommodating chip according to claim 2, wherein
a surface of the coating layer has hydrophilicity, a low cell adhesion property, and affinity to a specific binding material having affinity to a produced substance produced by a cell accommodated in one of the wells and/or a released substance released by the cell.

4. The cell accommodating chip according to claim 1, wherein the coating layer having the low cell adhesion property is a coating layer including a low cell adhesive material.

5. The cell accommodating chip according to claim 3, wherein the coating layer having the low cell adhesion property is a coating layer including a low cell adhesive material.

6. The cell accommodating chip according to claim 4, wherein the low cell adhesive material is a low protein adsorption material.

7. The cell accommodating chip according to claim 5, wherein the low cell adhesive material is a low protein adsorption material.

8. The cell accommodating chip according to claim 3, wherein the coating layer having affinity to the specific binding material is a coating layer including a binding material having affinity to the specific binding material.

9. The cell accommodating chip according to claim 3, wherein the coating layer having the hydrophilicity is a coating layer including a hydrophilic material.

10. The cell accommodating chip according to claim 8, wherein the binding material is a functional group-containing material having at least one functional group selected from an active ester group, a carboxyl group, a thiol group, an aldehyde group, a hydrazino group, a hydroxylamino group, and a bromoacetyl group.

11. The cell accommodating chip according to claim 8, wherein the binding material is at least one selected from streptavidin, avidin, biotin, and derivatives thereof.

12. The cell accommodating chip according to claim 6, wherein the low protein adsorption material is a polymer compound.

13. The cell accommodating chip according to claim 7, wherein the low protein adsorption material is a polymer compound.

14. The cell accommodating chip according to claim 1, wherein the cell accommodating chip is used in a screening apparatus for searching for a predetermined cell based on optical information emitted from a substance on the cell accommodating chip and selectively collecting the cell searched for.

15. The cell accommodating chip according to claim 1, wherein the binding material comprises avidin.

16. The cell accommodating chip according to claim 1, wherein an average value of a contact angle of the surface having the coating layer of the cell accommodating chip is 50° to 60°.

17. The cell accommodating chip according to claim 1, wherein the coating layer includes PEG or its derivative.

18. A screening method for searching for a predetermined cell based on optical information emitted from a substance on a cell accommodating chip and selectively picking up the cell searched for, the method comprising:

a preparation step of preparing a cell accommodating chip having a plurality of wells disposed on a substrate composed of a light-transmitting material and having a surface having a low cell adhesion property and affinity to a specific binding material having affinity to a produced substance produced by a cell accommodated in one of the wells and/or a released substance released by the cell, wherein a coating layer is on the substrate;
wherein a contact angle of the surface having the coating layer of the cell accommodating chip is less than or equal to 60°;
wherein the coating layer is formed on the inner surface of each of the wells and at least the main face with the wells of the substrate, and each of the wells has a size corresponding to accommodation of a single cell;
a first binding step of binding the specific binding material to the surface of the cell accommodating chip prepared in the preparation step;
a cell accommodating step of introducing a liquid containing a plurality of cells to the cell accommodating chip and accommodating the plurality of cells in the plurality of wells on a cell-by-cell basis;
a second binding step of binding a produced substance and/or a released substance by the cell accommodated in one of the wells to the specific binding material;
a third binding step of binding the produced substance or the released substance or the specific binding material to an optical information-holding substance having optical information;
a measurement step of measuring the optical information of the optical information-holding substance; and
an identification/collection step of identifying and collecting a cell as a target sample from the plurality of cells based on the measurement result in the measurement step.

19. The screening method according to claim 18, wherein an average value of a contact angle of the surface having the coating layer of the cell accommodating chip is 50° to 60°.

20. The screening method according to claim 18, wherein the coating layer includes PEG or its derivative.

21. A cell accommodating chip for accommodating a plurality of cells, comprising:
a substrate made of a light-transmitting material; and
a plurality of wells capable of accommodating cells on at least one main surface of the substrate, wherein
the surface of the cell accommodating chip having the plurality of wells has:
a low cell adhesion property; and
affinity to a specific binding material having affinity to a generated substance generated by a cell accommodated in any of the wells and/or a released substance released by the cell,
a coating layer on the substrate, wherein
a surface of the coating layer has hydrophilicity, a low cell adhesion property, and affinity to the specific binding material having affinity to a generated substance generated by a cell accommodated in any of the wells and/or a released substance released by the cell, and
the coating layer having affinity to the specific binding material is a coating layer including a binding material having affinity to the specific binding material, and
the binding material is a functional group-containing material having at least one functional group selected from an active ester group, a carboxyl group, a thiol group, an aldehyde group, a hydrazino group, a hydroxylamino group, and a bromoacetyl group, or the binding material is at least one selected from streptavidin, avidin, biotin, and derivatives thereof, and wherein a contact angle of the surface having the coating layer of the cell accommodating chip is less than or equal to 60°, wherein the coating layer is formed on the inner surface of each of the wells and at least the main face with the wells of the substrate, and each of the wells has a size corresponding to accommodation of a single cell, and wherein the binding material is not bound to the specific binding material.

22. The cell accommodating chip according to claim 21, wherein the binding material comprises avidin.

23. The cell accommodating chip according to claim 21, wherein an average value of a contact angle of the surface having the coating layer of the cell accommodating chip is 50° to 60°.

24. The cell accommodating chip according to claim 21, wherein the coating layer includes PEG or its derivative.

* * * * *